US006927294B1

(12) United States Patent
Petasis et al.

(10) Patent No.: US 6,927,294 B1
(45) Date of Patent: Aug. 9, 2005

(54) NITROGEN-CONTAINING HETEROCYCLES

(75) Inventors: Nicos A. Petasis, Hacienda Heights, CA (US); Xin Yao, Guilderland, NY (US); Jeffrey C. Raber, Whittier, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 10/386,389

(22) Filed: Mar. 10, 2003

Related U.S. Application Data

(60) Provisional application No. 60/363,646, filed on Mar. 8, 2002.

(51) Int. Cl.$^7$ .................. C07D 221/02; C07D 211/40
(52) U.S. Cl. ................ 546/183; 546/219; 546/220
(58) Field of Search ............................. 546/183, 219, 546/220, 242

(56) References Cited

U.S. PATENT DOCUMENTS

| | | | | |
|---|---|---|---|---|
| 4,442,099 | A | 4/1984 | Nicolaou et al. | 424/248.57 |
| 4,567,290 | A | 1/1986 | Nicolaou et al. | 560/124 |
| 4,710,521 | A | 12/1987 | Soukup et al. | 521/118 |
| 4,759,880 | A | 7/1988 | Nicolaou et al. | 260/413 |
| 5,087,790 | A | 2/1992 | Petasis et al. | 585/638 |
| 5,136,501 | A | 8/1992 | Silverman et al. | 364/408 |
| 5,177,046 | A | 1/1993 | Savoca et al. | 502/167 |
| 5,276,120 | A * | 1/1994 | Wong et al. | 546/184 |
| 5,594,732 | A | 1/1997 | Bell et al. | 370/401 |
| 5,752,238 | A | 5/1998 | Dedrick | 705/14 |
| 5,756,789 | A | 5/1998 | Bruce et al. | 556/14 |
| 5,842,040 | A | 11/1998 | Hughes et al. | 395/831 |
| 5,845,265 | A | 12/1998 | Woolston | 705/37 |
| 5,870,717 | A | 2/1999 | Wiecha | 705/26 |
| 5,878,400 | A | 3/1999 | Carter, III | 705/20 |
| 5,878,423 | A | 3/1999 | Anderson et al. | 707/100 |
| 5,890,138 | A | 3/1999 | Godin et al. | 705/26 |
| 5,896,379 | A | 4/1999 | Haber | 370/390 |
| 5,946,467 | A | 8/1999 | Pathakis et al. | 395/200.66 |
| 6,030,715 | A | 2/2000 | Thompson et al. | 428/690 |
| 6,030,917 | A | 2/2000 | Weinberg et al. | 502/104 |
| 6,069,109 | A | 5/2000 | Kao et al. | 502/152 |
| 6,232,467 | B1 | 5/2001 | Petasis et al. | 544/171 |
| 6,259,699 | B1 | 7/2001 | Opalka et al. | 370/398 |
| 6,272,474 | B1 | 8/2001 | Garcia | 705/37 |
| 6,336,105 | B1 | 1/2002 | Conklin et al. | 705/80 |
| 6,336,138 | B1 | 1/2002 | Caswell et al. | 709/223 |
| 6,377,937 | B1 | 4/2002 | Paskowitz | 705/26 |
| 6,397,212 | B1 | 5/2002 | Biffar | 707/5 |
| 6,415,270 | B1 | 7/2002 | Rackson et al. | 705/37 |
| 6,427,132 | B1 | 7/2002 | Bowman-Amuah | 703/22 |
| 6,602,817 | B1 | 8/2003 | Petasis | 502/172 |
| 2003/0236423 | A1 | 12/2003 | Petasis | 554/61 |

FOREIGN PATENT DOCUMENTS

| | | |
|---|---|---|
| EP | 0 736 509 A2 | 10/1996 |
| EP | 0 736 509 B1 | 11/2001 |
| WO | WO 97/19415 | 5/1997 |
| WO | WO 98/19259 | 5/1998 |
| WO | WO 98/35469 | 8/1998 |
| WO | WO 99/06913 | 2/1999 |
| WO | WO 99/13417 | 3/1999 |

OTHER PUBLICATIONS

Nugent, William A., "Chiral Lewis Acid Catalysts. Enantioselective Addition of Azide to Meso Epoxides" J. Am. Chem. Soc., vol 114(7), pp. 2668–2769 (1992).*

Butters et al, "Molecular requirements of imino sugars for the selective control of N–linked glycosylation and glycosphingolipid biosynthesis" Tetrahedron: Asymmetry, vol. 11, pp. 113–124 (2000).*

Mao et al, "Synthesis of 1–deoxymannojirimycin analogues using N–tosyl and N–nosyl activated aziridines derived from 1–amino deoxyglucitol" Tetrahedron, vol. 57, pp. 6955–6967 (2001).* van den Broek et al, "Synthesis of oxygen–substituted N–alkyl 1–deoxynorjirimycin derivatives: aza sugar alpha–glucosidase inhibitors showing antiviral (HIV–1) and immunosuppressive activity" Recl. Trav. Chim. Pays–Bas, vol. 113(110) pp. 507–516 (1994).*

Shilvock et al, "Ihibition of Naringinase (L–Rhamnosidase) by Piperidine Analogues of L–Rhamnose: Scaffolds for Libraries Incorporating Trihydroxypipecolic acids" Tetrahedron Letters, vol. 37(47) pp. 8569–8572 (1996).*

Lee et al, Inhibition of UDP–Gal Mutase and Mycobacterial Galactan Biosynthesis by Pyrrolidine Analogues of Galactofuranos Tetrahedron Letters, vol. 38(38) pp. 6733–6736 (1997)*

Luna et al, "Stereoselective Ring Opening of meso Bicyclic Hydrazines: A Straightforward Approach to Hydrazino Cyclopenten Cores" Organic Letters, vol. 5(25), pp. 4771–4774 (2003).*

Babine, R. E. and S.L. Bender., "Molecular Recognition of Protein–Ligand Complexes: Applications to Drug Design," Chem. Rev. 97:1359–1472 (1997).

Bhaley, G. et al., "Solid–Phase Synthesis of Diverse Tetrahydro–1,4–Benzodiazepine–2–ones," Tetrahedron Letters 38(48):8375–8378 (1997).

Bläser, E. et al., "Asymmetric Steering of Oxa Diels—Alder Reactions with Silyloxydienes Employing Proline Esters as Chiral Auxiliary Groups," Eur. J. Org. Chem., 329–333, (1999).

Deloux, Laurent and Morris Srebnik "Asymmetric Boron–Catalyzed Reactions", Chem. Rev. 93:763–784, (1993).

(Continued)

Primary Examiner—James O. Wilson
Assistant Examiner—Zachary C. Tucker
(74) Attorney, Agent, or Firm—Fish & Richardson P.C.

(57) ABSTRACT

Functionalized nitrogen heterocyclic compounds, including benzodiazepines and azasugars, and synthetic methods for preparing such compounds. Nitrogen-containing heterocycles are prepared by reacting amino-carbonyl compounds that contain an amine moiety connected via a linker to a carbonyl moiety with an organoboron derivative.

3 Claims, No Drawings

OTHER PUBLICATIONS

Durantel. et al., "Study of the Mechanism of Antiviral Action of Iminosugar Derivatives against Bovine Viral Diarrhea Virus," *J. Virology* 75(19): 8987–8998, (2001).

Du Bois, et al., "Novel, Stereoselective Synthesis of 2–Amino Saccharides," *J. Am. Chem. Soc.* 119:3179–3180, 1997.

Evans, B.E. et al., "Design of Nonpeptidal Ligands for a Peptide Receptor: Cholecystokinin Antagonists," *J. Med. Chem.* 30:1229–1239 (1987).

Fletcher, M. D. and M.C. Campbell, "Partially Modified Retro–Inverso Peptides: Development, Synthesis, and Conformational Behavior," *Chem. Rev.*, 98:763–795, (1998).

Garro–Helion, et al., "Mild and Selective Palladium(0)–Catalyzed Deallylation of Allylic Amines. Allylamine and Diallylamine as Very Convenient Ammonia Equivalents for the Synthesis of Primary Amines," *J. Org. Chem.*, 58:6109–6113, (1993).

Golebiowski, A. and J. Jurczak, "α–Amino–β–hydroxy Acids in the Total Synthesis of Amino Sugars," *Synlett*, pp. 241–245, (Apr., 1993).

Guillier et al., "Linkers and Cleavage Strategies in Solid–Phase Organic Syntheis and Combinatorial Chemistry," *Chem. Rev.*, 100:2091–2157, (2000).

Hanessian, S. et al., "Design and Synthesis of Conformationally Constrained Amino Acids as Versatile Scaffolds and Peptide Manners," *Tetrahedron*, 53:12789–12854, (1997).

Hoyng, C.F. and A.D. Patel, "Aldehyde Components for Use in Four–Component Condensation ("4CC") UGI Reaction Peptide Synthesis," *Tetrahedron Lett.*, 21:4795–4798, (1980).

Humphrey, J.M. and A.R. Chamberlin, "Chemical Synthesis of Natural Product Peptides: Coupling Methods for the Incorporation of Noncoded Amino Acids into Peptides," *Chem. Rev.*, 97:2243–2266, (1997).

König et al., "Synthesis of N–tert–Alkylglyoxylic Acid Amides," *Synthesis*, pp. 1233–1234, (1993) [in German, English language abstract on 1$^{st}$ page of article].

Marx et al., "Synthetic Design for Combinatorial Chemistry. Solution and Polymer–Supported Synthesis of Polycyclic Lactams by Intramolecular Cyclization of Azomethine Ylides," *J. Am. Chem. Soc.*, 119:6153–6167, (1997).

Mehta et al., "Structure–Activity Relationship of a New Class of Anti–Hepatitis B Virus Agents," *Antimicrobial Agents and Chemotherapy*, 46(12);4004–4008 (2002).

Nicolaou et al., "Novel IBX–Mediated Process for the Synthesis of Amino Sugars and Libraries Thereof," *Angew. Chem. Int. Ed. Engl.*, 39:2525–2529, (2000).

Nicolaou, et al., "Lipoxins and Related Eicosanoids: Biosynthesis, Biological Properties, and Chemical Synthesis," *Angew. Chem. Int. Ed. Engl.* 30:1100–1116, (1991).

Noyori, R. (Ed.), "Enantioselective Addition of Organometallic Reagents to Carbonyl Compounds: Chirality Transfer, Multiplication, and Amplification," Chapter 5 in *Asymmetrical Catalysis in Organic Synthesis*, New York: John Wiley & Sons, Inc., pp. 255–297 (1994).

O'Donnell, Martin J. and J. Falmagne, "The Synthesis of Amino Acids via Organoboranes." *J. Chem. Soc. Chem. Commun.*, No. 17, pp. 1168–1169, (Sep. 1, 1985).

Petasis, N. A. and I.A. Zavialov, "The Boronic Acid Mannich Reaction: A New Method for the Synthesis of Geometrically Pure Allylamines." *Tetrahedron Letters*, 34(4):583–386, (1993).

Petasis, N.A. and I.A. Zavialov, "A New and Practical Synthesis of α–Amino Acids from Alkenyl Boronic Acids," *J. Am. Chem. Soc.*, 119(2):445–446, (1997).

"Scope and Editorial Policy," *Organometallics*, published by the American Chemical Society 21(1):13A, 14A (2002).

Serhan et al., "Novel Functional Sets of Lipid–derived Mediators with Antiinflammatory Actions Generated from Omega–3 Fatty Acids via Cyclooxygenase 2–Nonsteroidal Antiinfammatory Drugs and Transcellular Processing," *J. Exp. Med.* 192:1197–1204, (2000).

Thompson, L.A. and J.A. Ellman, "Synthesis and Applications of Small Molecule Libraries," *Chem. Rev.* 96:555–600 (1996).

Waki, M. and J. Meienhofer, "Peptide Synthesis Using the Four–Component Condensation (Ugi Reaction)," *J. Am. Chem. Soc.*, 99:6075–6082, (1977).

Yamamoto, Y. and N. Asao, "Selective Reactions Using Allylic Metals." *Chem. Rev.*, 93:2207–2293, (1993).

* cited by examiner

NITROGEN-CONTAINING HETEROCYCLES

CROSS REFERENCE TO RELATED APPLICATIONS

This application claims the benefit of U.S. Provisional Application No. 60/363,646, filed on Mar. 8, 2002, which is incorporated herein by reference in its entirety.

STATEMENT REGARDING FEDERALLY SPONSORED RESEARCH

The U.S. Government may have certain rights in this invention pursuant to Grant No. GM45970 awarded by the National Institutes of Health.

BACKGROUND

This invention relates to the fields of organic synthesis, organoboron chemistry, combinatorial chemistry and medicinal chemistry.

Heterocyclic derivatives containing one or more nitrogen atoms are exceedingly common in a large variety of pharmaceuticals and pharmaceutical intermediates. Such systems are often essential for the overall utility of molecules of this type, including their use as active pharmaceutical ingredients for the treatment of some of the most common diseases, including cancer, cardiovascular diseases, CNS diseases, etc.

Among the most widely known examples of heterocycles are several types of benzodiazepine derivatives which are widely used as pharmaceuticals. For several decades the benzodiazepine ring system has been one of the most effective scaffolds for the development of therapeutic agents. Among the various substitution patterns, most common are those present in such widely used anxiolytic agents as diazepam (Thompson, L. A; Ellman, J. A., *Chem. Rev.*, 1996, 96, 555), while less common are the structures present in various peptidomimetics (Evans, B. E.; et al., *J. Med. Chem.*, 1987, 30, 1229. Bhalay, G.; et al., *Tet. Lett.*, 1997, 38, 8375).

A large variety of nitrogen heterocycles occur widely in nature and many variants of these have found applications as active pharmaceutical ingredients. For example, azasugars, such as polyhydroxylated piperidine, indolizine and quinolizidine alkaloids have attacted considerable interest in recent years because they exhibit potent glycosidase inhibitory activity, resulting in a wide range of pharmacological properties against cancer, HIV and other diseases (Stütz, A. E. *Iminosugars as Glycosidase Inhibitors, Nojirimycin and beyond*, Wiley-VCH, 1999). Several natural or synthetic azasugars have found applications as therapeutic agents, as a result of their behavior as glucosidase inhibitors and other bioactivities. For example n-butyl deoxynojirimycin and N-nonyl-deoxy-galactonojirimycin were shown to have potent antiviral activity against several viruses, including HIV and hepatitis B virus (D. Durantel, et al. *J. Virology*, (2001), p. 8987; A. Mehta, et al, *Ant. Agents and Chemoherapy*, 4004 (2002)).

SUMMARY

The invention provides functionalized nitrogen heterocyclic compounds, including benzodiazepines and azasugars, and synthetic methods for preparing such compounds. The invention is based in part on the discovery of a three-component reaction among an amine derivative, a carbonyl compound and an organoboron derivative, in which the amine and carbonyl components are joined together in a single molecule via a suitable linker.

In general, in one aspect, the invention features methods of preparing nitrogen heterocycles of formula 3. An amino-carbonyl compound 1 is reacted with an organoboron derivative 2, to form the nitrogen heterocycle 3.

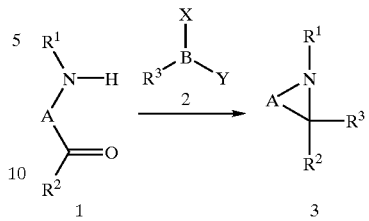

wherein:

$R^1$ is hydrogen, alkyl, aryl, heteroaryl, hydroxy, or alkoxy;

$R^2$ is hydrogen, alkyl, aryl, heteroaryl, or acyl;

$R^3$ is alkyl, aryl, heteroaryl, allyl, alkenyl, alkynyl, or allenyl, provided that $R^1$ and $R^3$ can be joined to form a ring of 5 to 10 atoms;

X and Y can be the same or different and are independently selected from a group consisting of hydroxy, alkoxy, aryloxy, amino, alkylamino, and dialkylamino; provided that substituents X and Y can also be joined together with a chain of up to 20 atoms defined similarly to linker A;

A is a linker that includes a chain of up to 20 atoms may include one or more nitrogen, oxygen, sulfur or phosphorous atoms, provided that linker A can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that linker A may also contain one or more fused rings, including carbocyclic, heterocyclic, aryl or heteroaryl rings;

provided that the carbonyl moiety in compound 1 can exist in a hemiacetal, hemiketal or aminal form, including cyclic variants;

the amine moiety in compound 1 can be present as the corresponding ammonium salt; and one or more of $R^1$, $R^2$, $R^3$, X, Y and linker A can be connected to a polymeric chain or other solid phase material.

Particular embodiments include one or more of the following features. The amino-carbonyl compound can be a compound of formulas 4 or 5, and the nitrogen heterocycle compound can be a benzodiazepine of formula 6

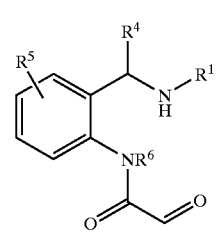

-continued

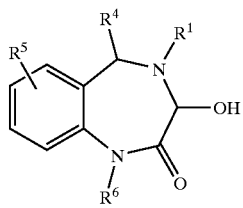

5

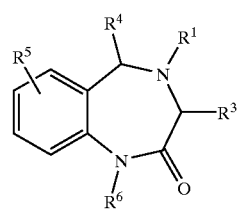

6 wherein:
- R⁴ is hydrogen, alkyl, aryl, heteroaryl, alkenyl, alkynyl, allenyl, acyl, carboxy, carboxamido or cyano;
- R⁵ is hydrogen, alkyl, aryl, heteroaryl, alkenyl, alkynyl, allenyl, acyl, carboxy, carboxamido or cyano, hydroxy, alkoxy, halo or nitro;
- R⁶ is hydrogen, alkyl, aryl, heteroaryl, hydroxy, or alkoxy;
- provided that one or more of R⁴, R⁵, and R⁶ can also be connected to a polymeric chain or other solid phase material; and
- the fused aryl ring can be replaced by a heteroaryl ring.

The amino-carbonyl compound can be a compound of formulas 20 or 21, and the nitrogen heterocycle compound can be an azasugar of formula 22

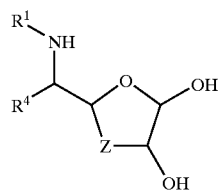

20

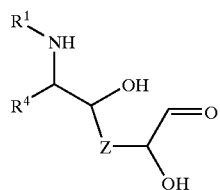

21

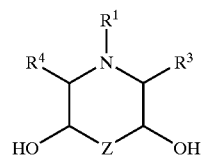

22 wherein:
- R⁴ is hydrogen, alkyl, aryl, heteroaryl, alkenyl, alkynyl, allenyl, acyl, carboxy, carboxamido or cyano;
- Z is a linker that includes of a chain of up to 20 atoms that may include one or more nitrogen, oxygen, sulfur or phosphorous atoms, provided that linker Z can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that linker Z may also contain one or more fused rings, including carbocyclic, heterocyclic, aryl or heteroaryl rings; and
- one or more of R⁴ and linker Z can also be connected to a polymeric chain or other solid phase material.

The compounds of formula 3, 6, or 22 can be subjected to subsequent transformations.

In general, in another aspect, the invention provides benzodiazepine derivatives of formula 6 and azasugar derivatives of formula 22

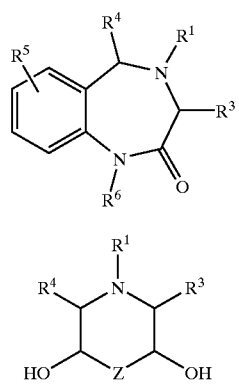

6

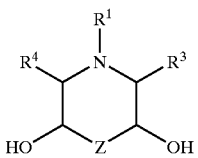

22 wherein:
- R¹ is hydrogen, alkyl, aryl, heteroaryl, hydroxy, or alkoxy;
- R³ is alkyl, aryl, heteroaryl, allyl, alkenyl, alkynyl, or allenyl, provided that R¹ and R³ can be joined to form a ring of 5 to 10 atoms;
- R⁴ is hydrogen, alkyl, aryl, heteroaryl, alkenyl, alkynyl, allenyl, acyl, carboxy, carboxamido or cyano;
- R⁵ is hydrogen, alkyl, aryl, heteroaryl, alkenyl, alkynyl, allenyl, acyl, carboxy, carboxamido or cyano, hydroxy, alkoxy, halo or nitro; and
- R⁶ is hydrogen, alkyl, aryl, heteroaryl, hydroxy, or alkoxy;
- Z is a linker that includes of a chain of up to 20 atoms that may include one or more nitrogen, oxygen, sulfur or phosphorous atoms, provided that linker Z can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that linker Z may also contain one or more fused rings, including carbocyclic, heterocyclic, aryl or heteroaryl rings;
- provided that in benzodiazepines 6, one or more of R¹, R³, R⁴, R⁵, and R⁶ can be connected to a polymeric chain or other solid phase material; and
- the fused aryl ring can be replaced by a heteroaryl ring; and
- further provided that in azasugars 22, one or more of R¹, R³, R⁴, and linker Z can also be connected to a polymeric chain or other solid phase material.

In particular embodiments, R³ is selected from aryl, heteroaryl, alkenyl, allyl and allenyl. In some embodiments, the azasugar 22 is a compound having a formula selected from the following:

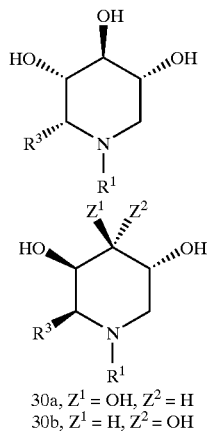

30a, $Z^1$ = OH, $Z^2$ = H
30b, $Z^1$ = H, $Z^2$ = OH

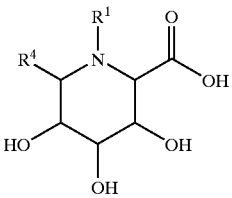

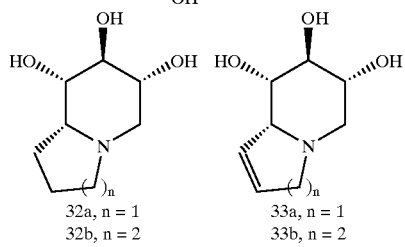

32a, n = 1
32b, n = 2

33a, n = 1
33b, n = 2

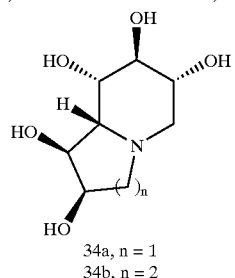

34a, n = 1
34b, n = 2

Particular embodiments of the invention can provide one or more of the following advantages. The synthetic methods of the invention provide an efficient and practical route to novel structures that are not readily available by other methods. The methods are highly versatile, allowing a high degree of structural variation in the reacting components. The methods allow the one-pot formation of complex heterocycles from several readily available building blocks. For these reasons, the methods are readily applicable to solid or liquid phase combinatorial synthesis.

The reactions with the organoboron derivatives can be carried out in water or aqueous solvents at ambient temperature. The reactions can be carried out without using toxic, hazardous or corrosive materials, such as cyanides, strong acids, strong bases, organotin, organocopper or other highly reactive organometallic compounds. The reactions do not require an inert atmosphere, and can be done in the air. In particular, the organoboronic acids used in some embodiments are often crystalline, easy to prepare and easy to handle compounds that are stable in air and water. They are also non toxic and non hazardous.

The heterocyclic products can be prepared using a smaller number of synthetic steps than most existing methods. Starting materials used in some of the reactions may be commercially available or can be readily prepared from commercially available reagents by a one-step procedure.

The stereochemical control of the reactions can be accomplished not only with the use of chiral amine and carbonyl components but also with chiral organoboron derivatives. Boron-based auxiliaries can be easily introduced and can be efficiently recycled after the reaction, thus making this method especially attractive for large scale applications. Due to the facile synthesis of alkenyl and aryl boron derivatives, which proceed with complete control of geometry or positional isomerism, isomerically pure products can be obtained.

The details of one or more embodiments of the invention are set forth in the description below. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. Other features and advantages of the invention will become apparent from the description and the claims.

DETAILED DESCRIPTION

Definitions:

An organoboron derivative, as defined herein, comprises a compound having a boron atom connected to at least one alkyl, allyl, alkenyl, aryl, allenyl or alkynyl group.

Alkyl groups of the present invention include straight-chained, branched and cyclic alkyl radicals containing up to about 20 carbons. Suitable alkyl groups may be saturated or unsaturated. Further, an alkyl may also be substituted one or more times on one or more carbons with substituents selected from the group consisting of C1–C6 alkyl, C3–C6 heterocycle, aryl, halo, hydroxy, amino, alkoxy and sulfonyl. Additionally, an alkyl group may contain up to 10 heteroatoms or heteroatom substituents. Suitable heteroatoms include nitrogen, oxygen, sulfur and phosphorous.

Aryl groups of the present invention include aryl radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

General Description:

Nitrogen heterocycle compounds 3 are prepared by reacting an amino-carbonyl compound 1, containing an amine moiety connected via a linker (A) to a carbonyl moiety, with an organoboron derivative 2, as illustrated in Scheme 1. This transformation is based on a C—C bond forming reaction among organoboron compounds and the adduct derived from a carbonyl and an amine. Without being bound by theory, it is believed that the C—C bond forming process involves the formation of an aminol, which reacts in situ with the boronic acid to give an ion pair consisting of an electrophilic iminium salt and a nucleophilic borate species. Finally, irreversible C—C bond formation with the extrusion of boric acid gives the heterocyclic product. A three component variant of this transformation is discussed in more detail in U.S. Pat. No. 6,232,467, which is incorporated by reference herein.

Scheme 1 wherein:

R$^1$ is hydrogen, alkyl, aryl, heteroaryl, hydroxy, or alkoxy;

R$^2$ is hydrogen, alkyl, aryl, heteroaryl, or acyl;

R$^3$ is alkyl, aryl, heteroaryl, allyl, alkenyl, alkynyl, or allenyl, provided that R$^1$ and R$^3$ can be joined to form a ring of 5 to 10 atoms;

X and Y can be the same or different and are independently selected from a group consisting of hydroxy, alkoxy, aryloxy, amino, alkylamino, and dialkylamino; provided that substituents X and Y can also be joined together with a chain of up to 20 atoms defined similarly to linker A;

A is a linker that includes a chain of up to 20 atoms may include one or more nitrogen, oxygen, sulfur or phosphorous atoms, provided that linker A can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that linker A may also contain one or more fused rings, including carbocyclic, heterocyclic, aryl or heteroaryl rings;

provided that the carbonyl moiety in compound 1 can exist in a hemiacetal, hemiketal or aminal form, including cyclic variants;

the amine moiety in compound 1 can be present as the corresponding ammonium salt; and one or more of R$^1$, R$^2$, R$^3$, X, Y and linker A can be connected to a polymeric chain or other solid phase materials.

Synthesis of Benzodiazepine Derivatives

According to one aspect of the invention, 1,4-benzodiazepin-2-ones 6 are produced by the reaction of amine-aldehydes 4 or aminals 5 with an organoboronic acid derivative 2, as shown in Scheme 2.

Scheme 2 wherein:

R$^1$ is hydrogen, alkyl, aryl, heteroaryl, hydroxy, or alkoxy;

R$^3$ is alkyl, aryl, heteroaryl, allyl, alkenyl, alkynyl, or allenyl, provided that R$^1$ and R$^3$ can be joined to form a ring of 5 to 10 atoms;

X and Y can be the same or different and are independently selected from the group consisting of hydroxy, alkoxy, aryloxy, amino, alkylamino, and dialkylamino, provided that substituents X and Y can also be joined together with a chain of up to 20 atoms;

R$^4$ is hydrogen, alkyl, aryl, heteroaryl, alkenyl, alkynyl, allenyl, acyl, carboxy, carboxamido or cyano;

R$^5$ is hydrogen, alkyl, aryl, heteroaryl, alkenyl, alkynyl, allenyl, acyl, carboxy, carboxamido or cyano, hydroxy, alkoxy, halo or nitro;

R$^6$ is hydrogen, alkyl, aryl, heteroaryl, hydroxy, or alkoxy;

provided that one or more of R$^1$, R$^3$, R$^4$, R$^5$, R$^6$, X, and Y can also be connected to a polymeric chain or other solid phase material; and the fused aryl ring can be replaced by a heteroaryl ring.

The desired derivatives 4 or 5 can be generated using standard methodologies as exemplified in Scheme 3, starting with Boc protection of o-aminomethyl aniline derivative 7 followed by acylation with an acrylic acid chloride derivative 9 to produce 10. Deprotection with HCl/AcOH, followed by neutralization gives 11, which undergoes reductive amination with an aldehyde (or ketone) leading to intermediate 12. The HCl salt 12 is subjected to ozonolysis, followed by work-up with Me$_2$S and neutralization with NaOH to give the amino-aldehyde 4/aminal 5. This product is directly reacted with a boronic acid derivative 2 to yield the desired benzodiazepin-2-one product 6, as shown in Scheme 2. The products 6 can be subsequently transformed to produce new compounds.

In some cases (e.g., reductive amination with benzaldehyde derivatives R1CHO), the reductive amination step can be followed by the subsequent steps that lead without intermediate isolation of products to final products 6, which can be isolated by filtration from the crude reaction mixture. As a result, the whole procedure can be carried out without purification of any of the intermediates, while still maintaining a high overall yield.

Scheme 3

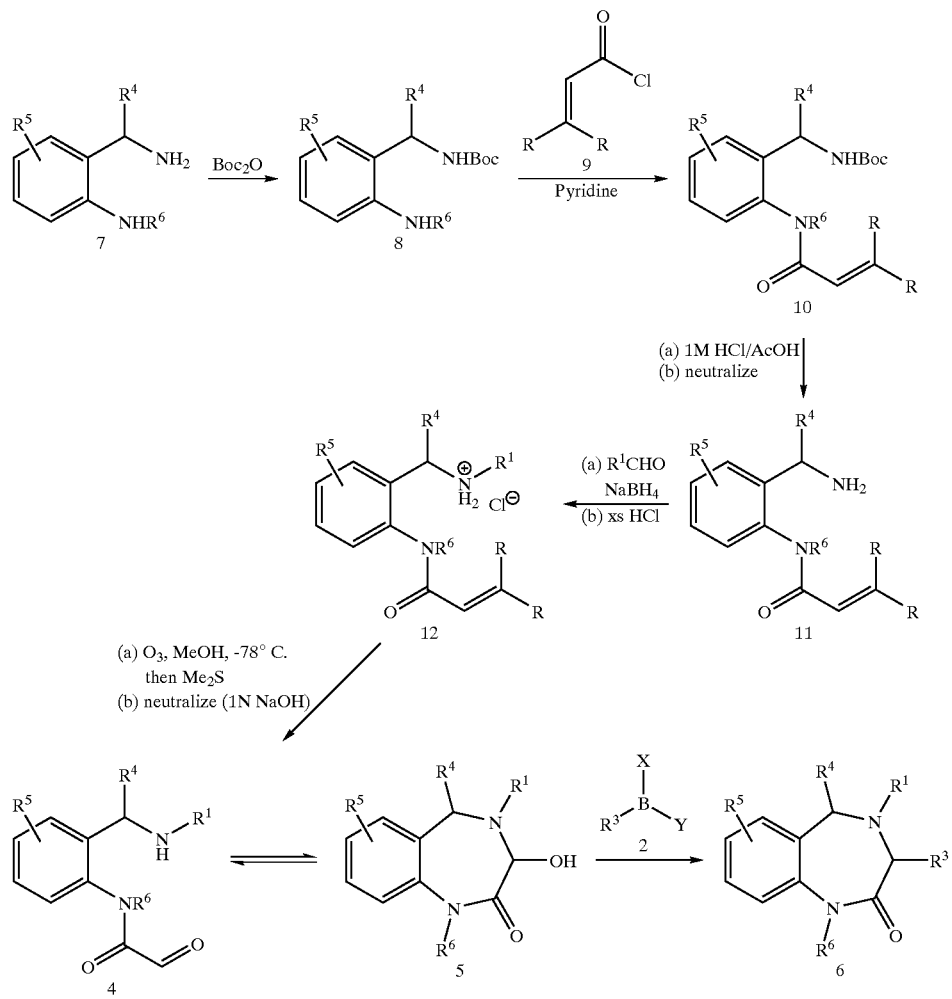

Alternatively, intermediates 12 can be obtained as shown in Scheme 4, by reductive amination with 2-amino phenone derivatives (e.g., 14) which can be produced by acylation of 13. Compound 4 can also be produced as outlined in Scheme 4, in a procedure not involving ozonolysis, thereby allowing the presence of cleavable functional groups, such as alkene moieties. Dihydroxylation of 14 gives 15, which after reductive amination to form 16 can be subjected to periodate cleavage to form 4. This methodology can be used for the synthesis of intermediates such as 17, having a alkene group at R1. Reaction of 17 with alkenyl boronic acids leads to 18, which can be subjected to ring-closing metathesis to form products having an additional ring system (e.g. 19).

Scheme 4

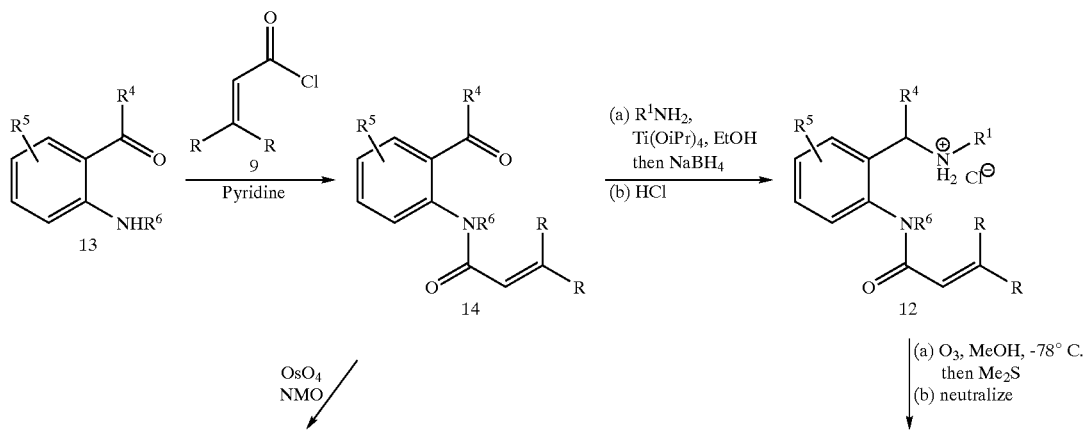

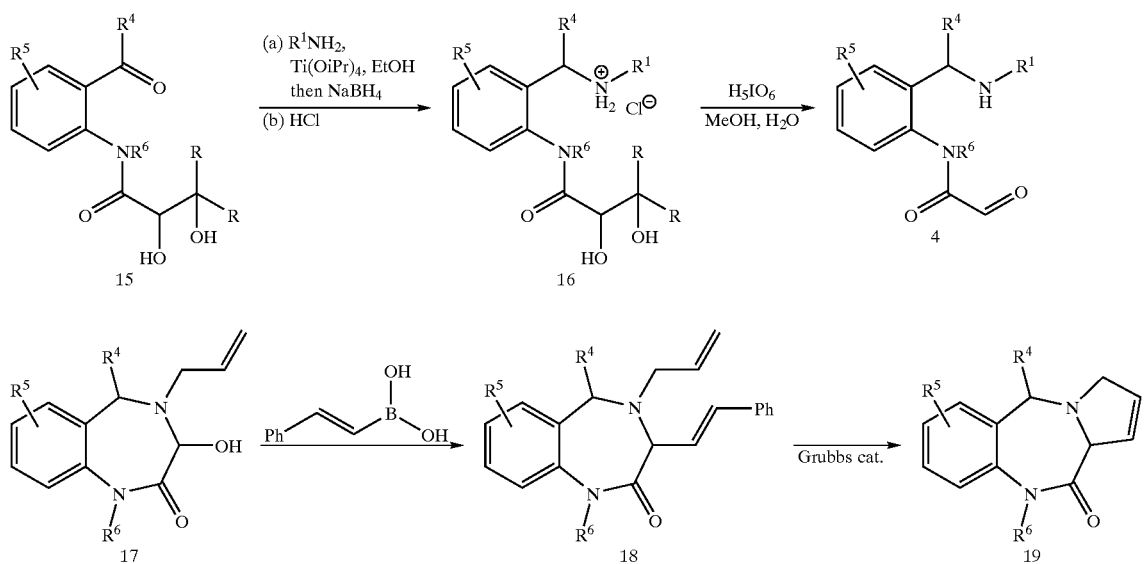

These methods allow for the short synthesis of novel substituted benzodiazepine derivatives and are directly suitable for the generation of combinatorial libraries of such compounds. This approach also allows the introduction of diverse functional groups by using various boronic acids and 1,3-diamines or amino benzophenones. The strategy is also applicable to the synthesis of novel peptidomimetic derivatives.

Some representative examples of benzodiazepin-2-ones that can be produced with this methodology are shown in Table 1.

TABLE 1

TABLE 1-continued

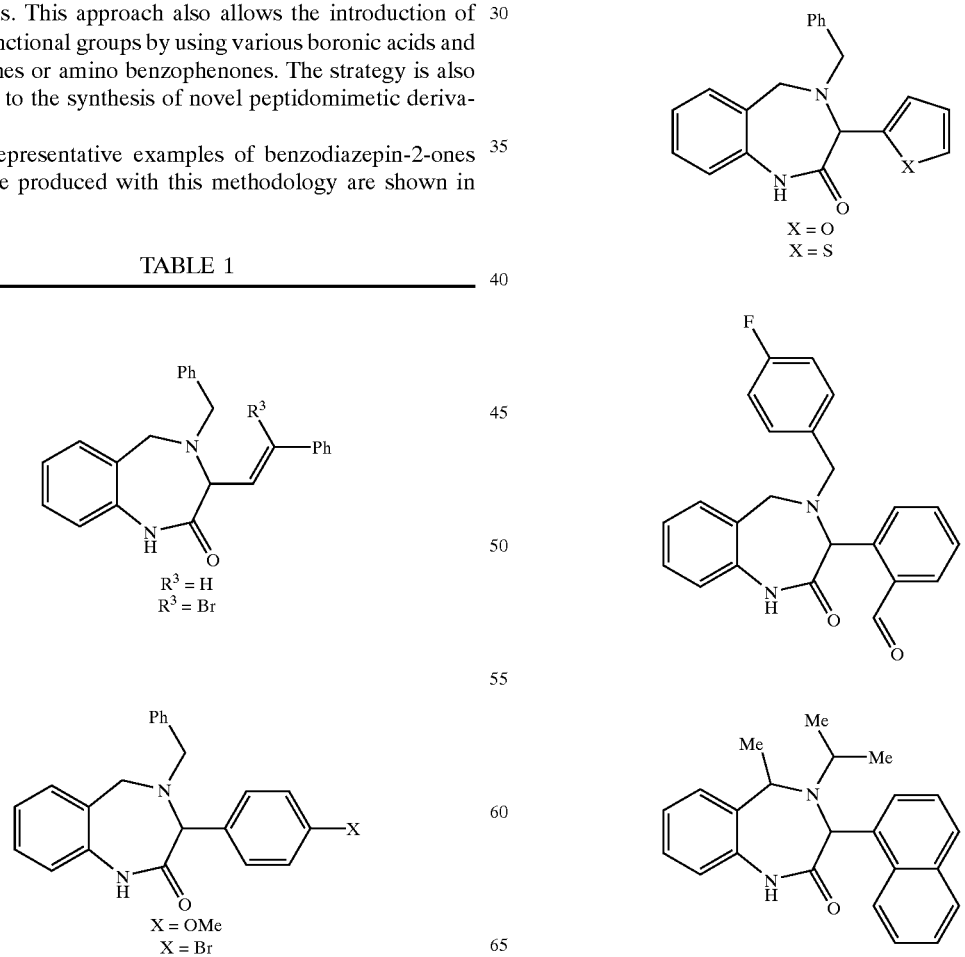

TABLE 1-continued

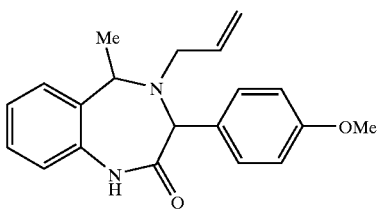

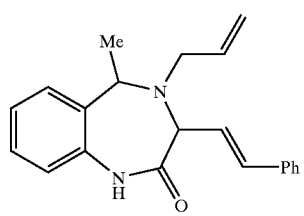

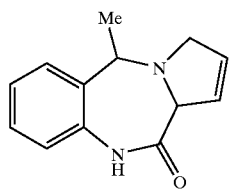

Synthesis of Azasugar Derivatives

According to another aspect of the invention, the techniques described herein can also be used for the synthesis of azasugar derivatives 22 via compound 20 or its open chain isomer 21, as outlined in Scheme 5.

Scheme 5

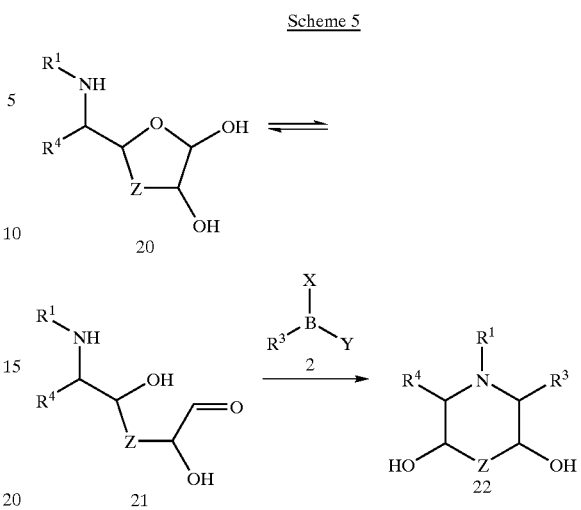

wherein:
R$^1$ is hydrogen, alkyl, aryl, heteroaryl, hydroxy, or alkoxy;
R$^3$ is alkyl, aryl, heteroaryl, allyl, alkenyl, alkynyl, or allenyl, provided that R$^1$ and R$^3$ can be joined to form a ring of 5 to 10 atoms;
X and Y can be the same or different and are independently selected from the group consisting of hydroxy, alkoxy, aryloxy, amino, alkylamino, and dialkylamino, provided that substituents X and Y can also be joined together with a chain of up to 20 atoms;
R$^4$ is hydrogen, alkyl, aryl, heteroaryl, alkenyl, alkynyl, allenyl, acyl, carboxy, carboxamido or cyano; and
Z is a linker that includes of a chain of up to 20 atoms that may include one or more nitrogen, oxygen, sulfur or phosphorous atoms, provided that linker Z can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that linker Z may also contain one or more fused rings, including carbocyclic, heterocyclic, aryl or heteroaryl rings;
provided that one or more of R$^1$, R$^3$, R$^4$, X, Y and linker Z can also be connected to a polymeric chain or other solid phase material; and
the amine moiety in compounds 20 or 21 can be present as the corresponding ammonium salt.

Compounds 20 or 21 can be prepared in a variety of ways, as outlined in Scheme 6.

Scheme 6

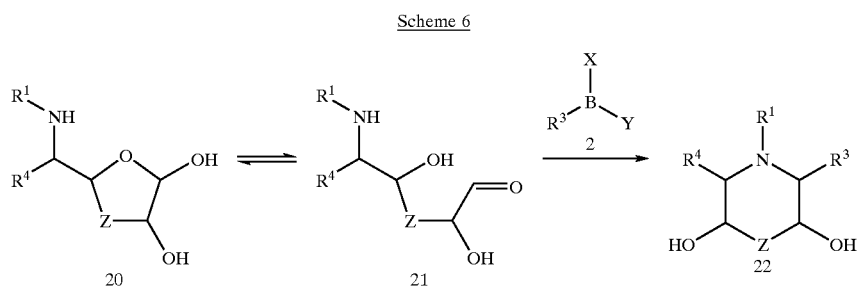

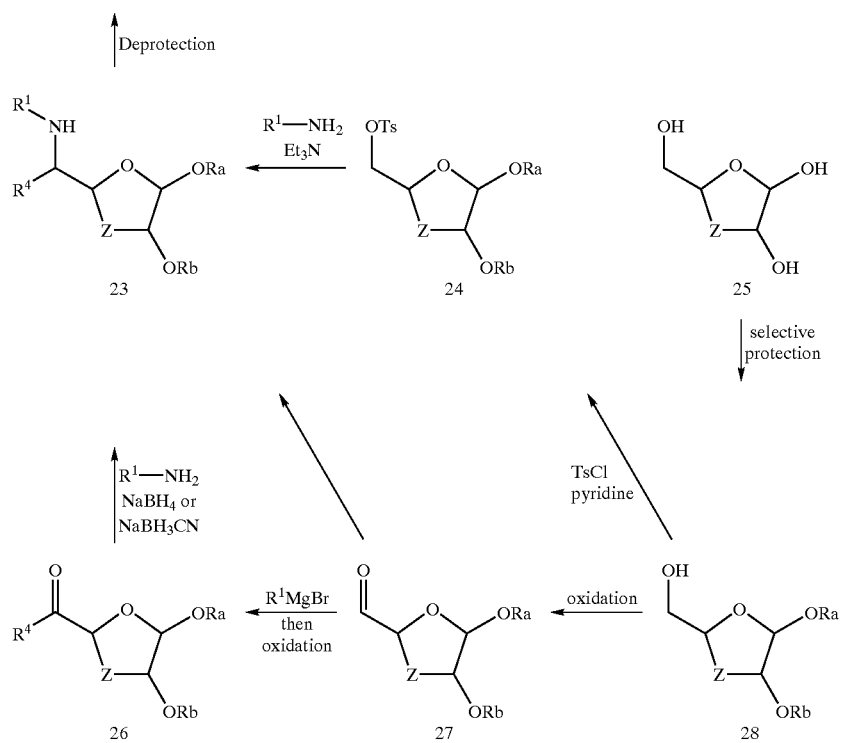

Thus, compounds 20 can be readily prepared via the incorporation of the amine moiety onto a suitably protected carbohydrate derivative to form 23, using known methods, as illustrated Scheme 6. For example, beginning with a sugar 25, selective protection followed by tosylation leads to 24, followed by amine incorporation to form 23 and deprotection under acidic conditions gives 20. Intermediate 23 can also be produced via the reductive amination of carbohydrate-like precursor 25 or 26. Aldehyde 27 can be formed via the oxidation of protected alcohol 28. A more substituted derivative (ketone 26) can be prepared from 27 via variety of known methods, such as addition of Grignard reagents and oxidation.

These methods allow for the short synthesis of novel substituted azasugars and is directly suitable for the generation of combinatorial libraries of such compounds. This approach also allows the introduction of diverse functional groups by using various boronic acids and starting sugars. The products 22 can be subsequently transformed to produce new compounds. Subsequent transformations of products 22 can lead to a variety of monocyclic or bicyclic derivatives, including the types of compounds shown in Table 2. For example, these techniques can be used to generate azasugars 29 and 30, pipecolic acids 31, indolizidines 32a, 33a or 34a and quinolizidines 32b, 33b or 34b. Since the reactions proceed in a stereospecific manner, compounds of types 29–34 can be produced in enantiomerically pure form, beginning with particular sugar starting materials.

TABLE 2

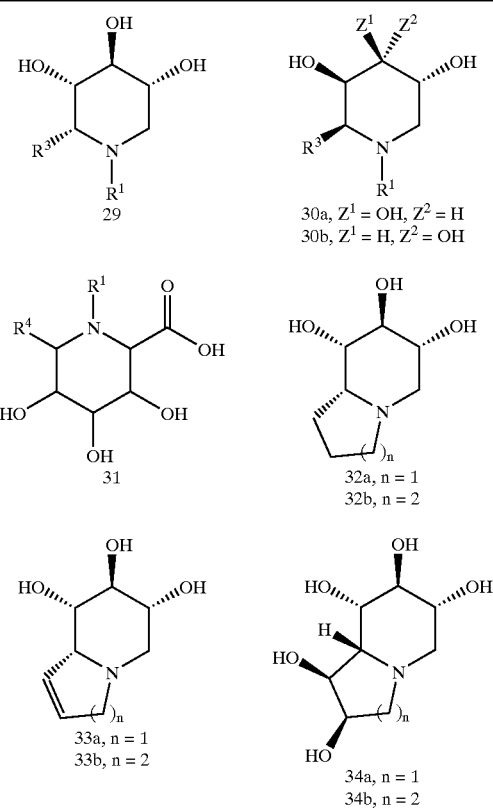

Benzodiazepine and Azasugar Derivatives

In another aspect, the invention features nitrogen-containing heterocyclic compounds, and in particular benzodiazepine and azasugar derivatives.

Thus, the compounds of the invention include benzodiazepines 6, which can be prepared according to the synthetic methods described above:

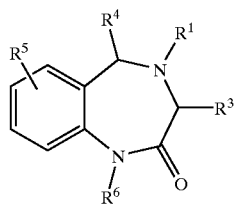

6 wherein:
- $R^1$ is hydrogen, alkyl, aryl, heteroaryl, hydroxy, or alkoxy; $R^3$ is alkyl, aryl, heteroaryl, allyl, alkenyl, alkynyl, or allenyl, provided that $R^1$ and $R^3$ can be joined to form a ring of 5 to 10 atoms;
- $R^4$ is hydrogen, alkyl, aryl, heteroaryl, alkenyl, alkynyl, allenyl, acyl, carboxy, carboxamido or cyano;
- $R^5$ is hydrogen, alkyl, aryl, heteroaryl, alkenyl, alkynyl, allenyl, acyl, carboxy, carboxamido or cyano, hydroxy, alkoxy, halo or nitro;
- $R^6$ is hydrogen, alkyl, aryl, heteroaryl, hydroxy, or alkoxy;
- provided that one or more of $R^1$, $R^3$, $R^4$, $R^5$, and $R^6$ can be connected to a polymeric chain or other solid phase material; and
- the fused aryl ring can be replaced by a heteroaryl ring.

In particular embodiments, the compounds of the invention include the benzodiazepin-2-ones identified in Table 1, above, and additional compounds set out in the examples, below.

Similarly, the compounds of the invention include azasugar derivatives 22, which can be prepared according to the synthetic methods described above:

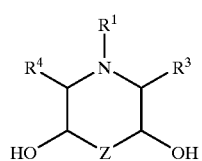

22 wherein:
- $R^1$ is hydrogen, alkyl, aryl, heteroaryl, hydroxy, or alkoxy;
- $R^3$ is alkyl, aryl, heteroaryl, allyl, alkenyl, alkynyl, or allenyl, provided that $R^1$ and $R^3$ can be joined to form a ring of 5 to 10 atoms;
- $R^4$ is hydrogen, alkyl, aryl, heteroaryl, alkenyl, alkynyl, allenyl, acyl, carboxy, carboxamido or cyano; and
- Z is a linker that includes of a chain of up to 20 atoms that may include one or more nitrogen, oxygen, sulfur or phosphorous atoms, provided that linker Z can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that linker Z may also contain one or more fused rings, including carbocyclic, heterocyclic, aryl or heteroaryl rings;
- provided that one or more of $R^1$, $R^3$, $R^4$, and linker Z can also be connected to a polymeric chain or other solid phase material.

In particular embodiments, the compounds of the invention include the azasugars 29 and 30, pipecolic acids 31, indolizidines 32a, 33a or 34a and quinolizidines 32b, 33b or 34b identified in Table 2, above, and additional compounds set out in the examples, below.

The invention will be further described in the following examples, which are illustrative only, and which are not intended to limit the scope of the invention described in the claims.

EXAMPLES

In the following examples, efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

3-Methyl-but-2-enoic acid (2-aminomethyl-phenyl)-amide

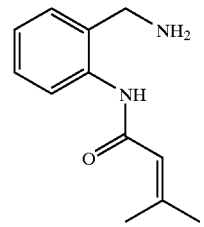

To a solution of 2-aminobenzylamine (2.440 g, 20.0 mmol) in dry dichloromethane (30 mL) was added a solution of di-tert-butyl dicarbonate (4.360 g, 20.0 mmol) in dry dichloromethane (12 mL) dropwise at room temperature over a few minutes. The reaction was then allowed to proceed until it was deemed complete by TLC (ethyl acetate-:hexane 1:1, 30 min.). The volatiles were removed and the resulting solid was purified by flash column chromatography using ethyl acetate-hexanes (1.5:8.5 to 3:7), affording 3.912 g of N-(-tert-butoxycarbonyl)-2-aminobenzylamine as an off-white powder (88%), which gave satisfactory spectroscopic and analytical data. This compound (1.333 g, 6.0 mmol) was placed dissolved in dry dichloromethane (20 mL) was reacted under dry conditions with 3,3-dimethylacrolyl chloride (0.67 mL, 6.06 mmol) and distilled pyridine (0.72 mL, 6.06 mmol). The mixture was then brought to reflux, and maintained at that temperature for 2 hrs. After this time, the mixture was cooled to room temperature and diluted with ethyl acetate (25 mL) and transferred to a separatory funnel with additional ethyl acetate (10 mL). The organic layer was then washed with 2N HCl (2×15 mL), and then carefully washed with saturated sodium bicarbonate (2×20 mL), and finally washed with brine (2×15 mL). The organic solution was then dried over magnesium sulfate, filtered and evaporated to dryness. The crude resulting solid was then recrystallized using ethyl acetate-hexanes to yield 1.465 g of 2-(3-Methyl-but-2-enoylamino)-benzyl]-carbamic acid tert-butyl ester, a white solid (80% yield). This compound had satisfactory spectroscopic and analytical data. 2-(3-Methyl-but-2-enoylamino)-benzyl]-carbamic acid tert-butyl ester (914 mg, 3.0 mmol) was reacted with 15 mL of 1M HCl in acetic acid at room temperature for 2 hours. After this time 15 mL of toluene was added and the solvents were evaporated. An additional 20 mL of toluene was added and evaporated, and this was repeated as necessary until a solid was recovered. This solid was then suspended in 20 mL of ethyl acetate, 20 mL of 1N NaOH was added and the mixture was poured into a separatory funnel. The aqueous layer was removed and the organic layer was washed further with 1N NaOH (2×15 mL). The organic layer was dried over magnesium sulfate, filtered, and the volatiles removed to yield 3-Methyl-but-2-enoic acid (2-aminomethyl-phenyl)-amide (612 mg) as a yellow oil (quantitative yield). $^1$H NMR (360 MHz, CD$_3$OD) δ 7.66–7.13 (m, 4H), 6.00 (s, 1H), 4.01 (s, 2H), 2.21 (s, 3H), 1.96 (s, 3H); $^{13}$C NMR (90 MHz, CD$_3$OD) 169.4, 156.1, 137.6, 132.0, 131.3, 130.1, 128.4, 127.6, 118.6, 41.1, 27.6, 20.3.

Example 2

3-Methyl-but-2-enoic acid [2-(benzylamino-methyl)-phenyl]-amide

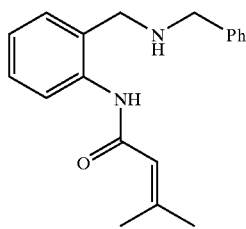

The product of Example 1 (612 mg, 3.0 mmol) was placed in a 25 mL round bottom flask and dissolved in methanol (6 mL). To this solution was added benzaldehyde (0.32 mL, 3.0 mmol) and the mixture was stirred at room temperature for 1 hr. After this time sodium borohydride (170 mg, 4.5 mmol) was added slowly over 10 minutes, and the mixture was allowed to stir for an additional 20 minutes. 15 mL of 1N NaOH was then added to quench the reaction, and the mixture was transferred to a separatory funnel with ethyl acetate. An additional 25 mL of ethyl acetate was added and the organic layer was washed successively with 1N NaOH (3×15 mL), brine (1×15 mL), and then dried over magnesium sulfate, filtered, and evaporated. The product was purified by flash column chromatography with ethyl acetate-hexane (3:7 then 1:1) to yield 3-methyl-but-2-enoic acid [2-(benzylamino-methyl)-phenyl]-amide (839 mg, 95% yield) of a yellow oil. $^1$H NMR (250 MHz, CDCl$_3$) 10.44 (s, 1H), 8.23 (d, J=8.0 Hz, 1H), 7.39–6.84 (m, 8H), 5.64–5.56 (m, 1H), 3.78 (s, 2H), 3.70 (s, 2H), 2.15 (s, 3H), 1.82 (s, 3H). The amine was then converted to the HCl salt with an excess of 1N HCl in ether to be used in further transformations.

Example 3

4-Benzyl-3-(4-methoxy-phenyl)-1,3,4,5-tetrahydro-benzo[e][1,4]diazepin-2-one

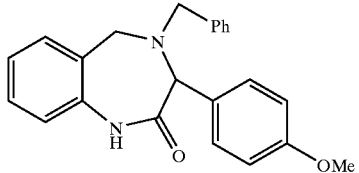

The HCl amine salt of Example 2 (132 mg, 0.4 mmol) was placed in a dry ozonolysis tube, and dissolved in an adequate amount of methanol. The tube was cooled to −78° C. and subjected to ozone until a blue color persisted. At this time, the tube was flushed with oxygen, and then an excess of dimethylsulfide (1.0 mL) was added. The solution was maintained at −78° C. for 30 minutes, brought to 0° C. and maintained there for an additional 30 minutes, and finally brought to room temperature and maintained there for an additional 1 hour. The volatiles were then removed and the residue suspended in ethyl acetate. 1N NaOH was added and stirred until a clear solution persisted. The mixture was then transferred to a separatory funnel with ethyl acetate, and the organic layer was washed with 1N NaOH (2×15 mL). The organic layer was dried with magnesium sulfate, filtered, and evaporated to yield an off-white solid. This solid was then placed in a round bottom flask, to which 5 mL of acetonitrile was added, followed by 4-Methoxyphenylboronic acid (76 mg, 0.5 mmol), the flask was equipped with a reflux condenser, and the mixture was brought to reflux and held there for 4 hours. After this time, the mixture was cooled to 0° C., and the resulting solid was filtered off, and washed with cold acetonitrile (10 mL) and vaccum dried to obtain 104 mg (73% yield) of a white fluffy solid. $^1$H NMR (360 MHz, CDCl$_3$) δ 7.65–7.55 (bs, 1H), 7.42–7.23 (m, 8H), 7.18–7.08 (m, 2H), 6.99 (d, J=7.8 Hz, 1H), 6.86 (d, J=8.6 Hz, 2H), 4.21 (s, 1H), 4.05 (d, J=13.2 Hz, 1H), 3.77 (s, 3H), 3.67–3.58 (m, 2H), 3.36 (d, J=13.2 Hz, 1H).

Example 4

4-Benzyl-3-(4-bromo-phenyl)-1,3,4,5-tetrahydro-benzo[e][1,4]diazepin-2-one

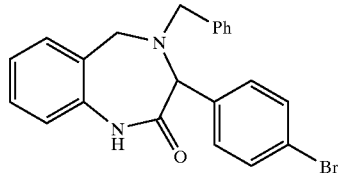

Prepared similarly to Example 3 in 60% yield. $^1$H NMR (360 MHz, CDCl$_3$) δ 7.58–7.51 (bs, 1H), 7.46–7.41 (m, 2H), 7.38–7.22 (m, 7H), 7.20–7.10 (m, 3H), 6.98 (d, J=8.0 Hz, 1H), 4.18 (s, 1H), 4.05 (d, J=13.5 Hz, 1H), 3.64 (d, J=14.5 Hz, 1H), 3.59 (d, J=14.5 Hz, 1H), 3.39 (d, J=13.5 Hz, 1H).

Example 5

4-Benzyl-3-(2-bromo-2-phenyl-vinyl)-1,3,4,5-tetrahydro-benzo[e][1,4]diazepin-2-one

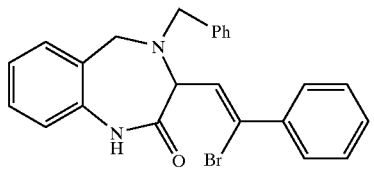

Prepared similarly to Example 3 in 65% yield. ¹H NMR (360 MHz, CDCl₃) δ 7.63–7.56 (bs, 1H), 7.48–7.17 (m, 13H), 7.60 (d, J=7.7 Hz, 1H), 6.53 (d, J=7.5 Hz, 1H), 4.21 (d, J=7.5 Hz, 1H), 3.92 (d, J=14.4 Hz, 1H), 3.82 (d, J=13.2 Hz, 1H), 3.64 (d, J=14.4 Hz, 1H), 3.57 (d, J=13.2 Hz, 1H).

Example 6

2-[4-(4-Fluoro-benzyl)-2-oxo-2,3,4,5-tetrahydro-1H-benzo[e][1,4]diazepin-3-yl]-benzaldehyde

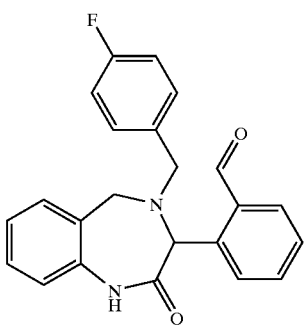

Prepared similarly to Example 3 with reductive amination using 4-fluorobenzaldehyde, and the use of 2-formylphenylboronic acid. Prepared in 34% overall yield without isolation of intermediates starting from the product of Example 1. ¹H NMR (500 MHz, DMSO-d₆) δ 10.37 (s, 1H), 7.83–7.79 (m, 1H), 7.64–7.60 (m, 1H), 7.40–7.34 (m, 2H), 7.29–7.19 (m, 3H), 7.70–6.95 (m, 5H), 6.32 (s, 1H), 5.09 (d, J=15.4 Hz, 1H), 5.01 (d, J=15.4 Hz, 1H), 4.56 (d, J=15.3 Hz, 1H), 4.47 (d, J=15.3 Hz, 1H).

Example 7

4Benzyl-3-styryl-1,3,4,5-tetrahydro-benzo[e][1,4]diazepin-2-one

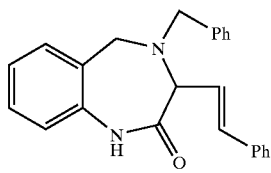

Prepared similarly to Example 3 in 63% yield. ¹H NMR (360 MHz, DMSO-d₆) δ 10.09 (s, 1H), 7.41–7.05 (m, 14H), 6.49 (d, J=16.1 Hz, 1H), 6.36 (dd, J=16.1, 7.3 Hz, 1H), 3.81 (d, J=14.3 Hz, 1H), 3.69 (d, J=14.3 Hz, 1H), 3.66 (d, J=7.3 Hz, 1H), 3.49 (d, J=13.7 Hz, 1H), 3.39 (d, J=13.7 Hz, 1H).

Example 8

4-Benzyl-3-furan-2-yl-1,3,4,5-tetrahydro-benzo[e][1,4]diazepin-2-one

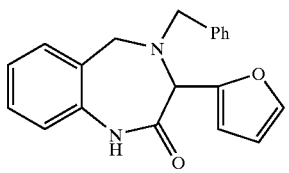

Prepared similar to Example 3 in 77% yield. ¹H NMR (360 MHz, DMSO-d₆) δ 10.17 (s, 1H), 7.58–7.53 (m, 1H), 7.39–7.23 (m, 6H), 7.15–7.03 (m, 3H), 6.37–6.28 (m, 2H), 4.30 (s, 1H), 3.81 (d, J=14.2 Hz, 1H), 3.58 (d, J=13.5 Hz, 1H), 3.52 (d, J=14.2 Hz, 1H), 3.49 (d, J=13.5 Hz, 1H).

Example 9

4-Benzyl-3-thiophen-2-yl-1,3,4,5-tetrahydro-benzo[e][1,4]diazepin-2-one

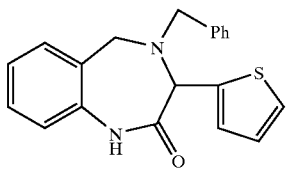

Prepared similar to Example 3 in 64% yield. ¹H NMR (360 MHz, DMSO-d₆) δ 10.17 (s, 1H), 7.58–6.74 (m, 12H), 4.41 (s, 1H), 3.86 (d, J=14.2 Hz, 1H), 3.54 (d, J=13.9 Hz, 1H), 3.47 (d, J=13.9 Hz, 1H), 3.34 (d, J=14.2 Hz, 1H).

Example 10

3-Methyl-but-2-enoic acid (2-acetyl-phenyl)-amide

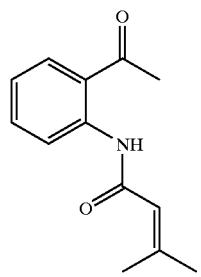

Prepared similarly to Example 1 via the acylation of 2-amino-benzophenone, in 72% yield. ¹H NMR (250 MHz, CDCl₃) δ 8.87–8.77 (m, 1H), 7.89–7.79 (m, 1H), 7.56–7.43 (m, 1H), 7.10–6.98 (m, 1H), 5.82–5.76 (m, 1H), 2.66–2.58 (m, 3H), 2.26–2.21 (m, 3H), 1.92 (s, 3H).

Example 11

3-Methyl-but-2-enoic acid [2-(1-isopropylamino-ethyl)-phenyl]-amide

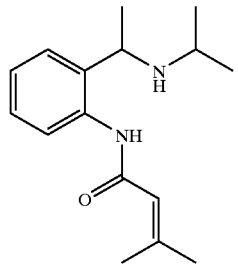

The product of Example 10 (217 mg, 1.0 mmol) was placed in a flame dried 25 mL round bottom flask, and flushed with Ar(g). The flask was charged with 8 mL of absolute ethanol, followed by isopropylamine (85.2 μL, 1.0 mmol), followed by the addition of titanium(IV) isopropoxide (0.59 mL, 2.0 mmol). The reaction was allowed to proceed at room temperature for 16 hours. After this time sodium borohydride (60 mg, 1.5 mmol) was added slowly over 10 minutes, and the mixture was allowed to stir for an additional 2 hours. The white precipitate was then filtered off, and washed with dichloromethane (20 mL). The washings were then collected, transferred to a separatory funnel, and washed successively with 1N NaOH (2×15 mL), and brine (1×15 mL). The organic layer was then dried over magnesium sulfate, filtered and evaporated to yield a crude oil, which was purified by column chromatography in ethyl acetate-hexane (3:7), to yield 216 mg of a yellow oil (83% yield). $^1$H NMR (360 MHz, CDCl$_3$) δ 8.46–8.36 (m, 1H), 7.26–7.17 (m, 1H), 7.07–7.00 (m, 1H), 6.99–6.90 (m, 1H), 5.70–5.66 (m, 1H), 4.08 (q, J=6.5 Hz, 1H), 2.71 (sep., J=6.5 Hz, 1H), 2.25 (d, J=0.8 Hz, 3H), 1.90 (d, J=1.2 Hz, 3H), 1.38 (d, J=6.5 Hz, 3H), 1.09 (d, J=6.5 Hz, 3H), 1.05 (d, J=6.5 Hz, 3H).

Example 12

4-Isopropyl-5-methyl-3-naphthalen-1-yl-1,3,4,5-tetrahydro-benzo[e][1,4]diazepin-2-one

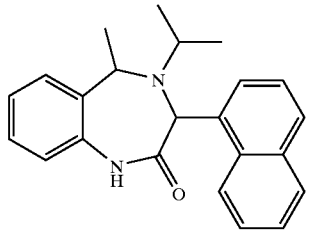

Prepared similarly to Example 3 starting with the product of Example 11, in 57% yield. $^1$H NMR (360 MHz, CDCl$_3$) δ 8.48–8.43 (m, 1H), 7.82–7.78 (m, 1H), 7.72 (d, J=8.1 Hz, 1H), 7.64–7.59 (bs, 1H), 7.55 (d, J=7.2 Hz, 1H), 7.45–7.39 (m, 2H), 7.32 (t, J=7.8 Hz, 1H), 7.18–7.12 (m, 2H), 7.05 (t, J=7.2 Hz, 1H), 6.73 (d, J=7.9 Hz, 1H), 5.66 (s, 1H), 4.35 (q, J=7.0 Hz, 1H), 2.92–2.79 (m, 1H), 1.49 (d, J=7.0 Hz, 3H), 1.05 (d, J=6.9 Hz, 3H), 0.97 (d, J=6.9 Hz, 3H).

Example 13

N-(2-Acetyl-phenyl)-2,3-dihydroxy-3-methyl-butyramide

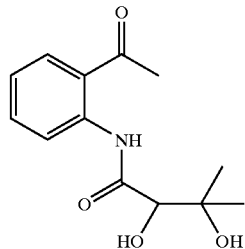

To the product of Example 10 (440 mg, 2.03 mmol) in acetone (4 mL) and H$_2$O (1 mL) was added 4-methylmorpholine N-oxide (269 mg, 2.23 mmol), and 2.5 wt % OsO$_4$ (0.25 mL, 0.02 mmol). The reaction mixture was stirred at room temperature for 26 h. EtOAc was added to the reaction mixture, and the resulting solution was washed with aqueous sodium bisulfite, brine and dried over MgSO$_4$. After evaporation of the volatiles, the crude product (505 mg, 99% yield) was clean enough to carry on the next step. $^1$H NMR (360 MHz, CDCl$_3$) δ 8.69–8.61 (m, 1H), 7.85–7.77 (m, 1H), 7.75–7.42 (m, 1H), 7.12–7.04 (m, 1H), 4.88 (d, J=5.4 Hz, 1H), 4.10 (s, 1H), 4.07 (d, J=5.4 Hz, 1H), 2.57 (s, 3H), 1.27 (s, 3H), 1.25 (s, 3H).

Example 14

N-[2-(1-Allylamino-ethyl)-phenyl]-2,3-dihydroxy-3-methyl-butyramide

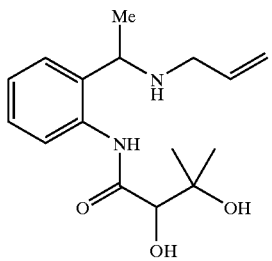

Prepared analogously to Example 11, starting with the product of Example 13 in 29% isolated yield (mixture of diastereomers), from flash column chromatography in ethyl acetate-hexane (3:2 to 4:1). $^1$H NMR (250 MHz, CDCl$_3$) δ 8.35–8.18 (m, 1H), 7.30–7.19 (m, 1H), 7.15–6.98 (m, 2H), 5.99–5.77 (m, 1H), 5.23–5.03 (m, 2H), 4.06–3.91 (m, 2H), 3.13 (d, J=5.6 Hz, 2H), 1.42 (d, J=6.7 Hz, 3H), 1.31 (s, 3H), 1.29 (d, J=2.5 Hz, 3H).

Example 15

4-Allyl-5-methyl-3-styryl-1,3,4,5-tetrahydro-benzo[e][1,4]diazepin-2-one

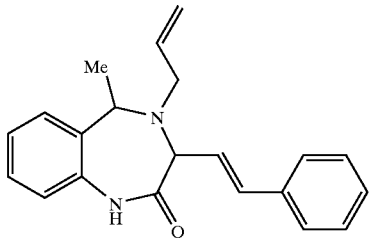

The product of Example 14 (117 mg, 0.4 mmol) was placed in a 25 mL round bottom flask and dissolved in methanol (2 mL) and water (1 mL). To this solution was added periodic acid (192 mg, 0.84 mmol), and the mixture was allowed to stir at room temperature for 2 hours. After this time, the solvent was then evaporated and the resulting residue was taken up in ethyl acetate (20 mL) and transferred to a separatory funnel. The organic layer was then washed with a saturated sodium bicarbonate solution (5×15 mL) until the aqueous layer no longer turned pink in color. The organic layer was then washed with brine (1×15 mL), dried over magnesium sulfate, filtered and evaporated. This resulting aminol was then dissolved in acetonitrile (4 mL) and to this solution was added (E)-2-Phenylvinylboronic acid (75 mg, 0.5 mmol), and the solution was brought to reflux for 4 hours. After this time, the reaction was diluted with ethyl acetate (40 mL), and transferred to a separatory funnel. The organic layer was washed with 1N NaOH (3×15 mL), brine (1×15 mL), dried over magnesium sulfate, filtered, and evaporated to yield the desired product, and an isomeric by-product in a combined yield of 81%. $^1$H NMR was used to estimate the ratio of product to by-product to be approximately 77:23. This mixture was taken crude to the next transformation to avoid further isomerization upon isolation. $^1$H NMR (250 MHz, CDCl$_3$, major isomer) δ 7.75 (bs, 1H), 7.43–7.37 (m, 2H), 7.33–7.15 (m, 6H), 7.11–7.04 (m, 1H), 6.85–6.82 (m, 1H), 6.57 (dd, J=16.0 Hz, J=4.8 Hz, 1H), 5.92–5.69 (m, 1H), 5.18–5.03 (m, 2H), 4.44–4.39 (m, 1H), 4.29 (q, J=6.6 Hz, 1H), 3.27–3.16 (m, 1H), 2.92–2.80 (m, 1H), 1.55 (d, J=6.6 Hz, 3H).

Example 16

5-Methyl-3,5,10,11a-tetrahydro-benzo[e]pyrrolo[1,2-a][1,4]diazepin-11-one

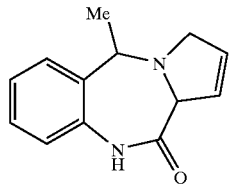

The product of Example 15 (103 mg, 0.32 mmol) was first converted to the HCl salt with excess 1M HCl in ether, and all of the volatiles were removed. The resulting solid was then dissolved in dry dichloromethane (15 mL) and bis(tricyclohexylphosphine)benzylidine ruthenium(IV) dichloride (132 mg, 0.16 mmol) was added, and the flask was flushed with Ar(g). The reaction was allowed to proceed at room temperature for three days, after which time, the reaction was diluted with an additional 10 mL of dichloromethane, and transferred to a separatory funnel. The organic layer was washed with a saturated solution of sodium bicarbonate (3×15 mL), the aqueous layers were then combined and extracted with dichloromethane (2×10 mL). The organic layers were then combined, washed once with brine (15 mL), dried over magnesium sulfate, filtered and evaporated to yield a crude residue which was purified by flash column chromatography using ethyl acetate-hexane (3:1) to yield 32 mg (61% yield) of a dark oil. $^1$H NMR (360 MHz, CDCl$_3$) δ 7.60 (bs, 1H), 7.42 (d, J=7.6 Hz, 1H), 7.32–7.19 (m, 2H), 7.00–6.95 (m, 1H), 6.16–6.10 (m, 1H), 5.88–5.82 (m, 1H), 4.34 (bs, 1H), 3.96–3.81 (m, 2H), 3.55–3.46 (m, 1H), 1.58 (d, J=6.5 Hz, 3H).

Example 17

4-Allyl-5-methyl-3-naphthalen-1-yl-1,3,4,5-tetrahydro-benzo[e][1,4]diazepin-2-one

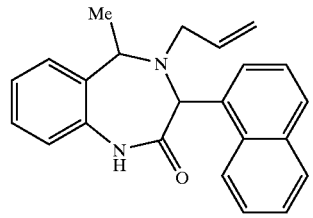

Prepared similar to Example 15 in 57% yield. $^1$H NMR (360 MHz, CDCl$_3$) δ 8.48–8.43 (m, 1H), 7.82–7.78 (m, 1H), 7.72 (d, J=8.1 Hz, 1H), 7.64–7.59 (bs, 1H), 7.55 (d, J=7.2 Hz, 1H), 7.45–7.39 (m, 2H), 7.32 (t, J=7.8 Hz, 1H), 7.18–7.12 (m, 2H), 7.05 (t, J=7.2 Hz, 1H), 6.73 (d, J=7.9 Hz, 1H), 5.66 (s, 1H), 4.35 (q, J=7.0 Hz, 1H), 2.92–2.79 (m, 1H), 1.49 (d, J=7.0 Hz, 3H), 1.05 (d, J=6.9 Hz, 3H), 0.97 (d, J=6.9 Hz, 3H).

Example 18

4-Allyl-3-(4-methoxy-phenyl)-5-methyl-1.3,4,5-tetrahydro-benzo[e][1,4]diaze-pin-2-one

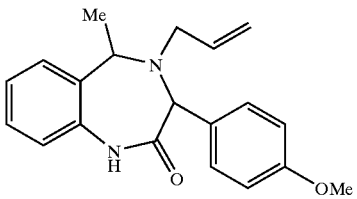

Prepared similar to Example 15 in 72%. $^1$H NMR (360 MHz, CDCl$_3$) δ 8.88 (s, 1H), 7.35–7.29 (m, 2H), 7.13–7.07 (m, 2H), 7.02–6.95 (m, 1H), 6.92–6.87 (m, 1H), 6.80–6.75 (m, 2H), 5.79–5.65 (m, 1H), 5.10–4.97 (m, 2H), 4.72 (s, 1H), 4.16 (q, J=6.8 Hz, 1H), 3.71 (s, 3H), 3.11–3.01 (m, 1H), 2.85–2.75 (m, 1H), 1.33 (d, J=6.8 Hz, 3H).

Example 19

1,2-Isopropylidene-5-p-toluenesulfonyl-α-D-xylofuranose

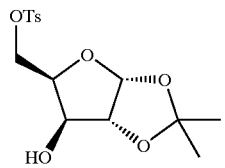

To a stirred solution of 1,2-O-isopropylidene-D-xylofuranose (1.978 g, 10.30 mmol) in dichloromethane (15 mL) was added DMAP (63 mg, 0.52 mmol), Et$_3$N (2.87 ml, 20.59 mmol), the solution was then cooled to 0° C. TsCl (2.022 g, 10.50 mmol) in dichloromethane (5 mL) was cannulated to the above solution. Reaction mixture was slowly warmed to room temperature overnight. Reaction mixture was diluted with EtOAc, washed with 2N HCl, saturated NaHCO$_3$, and saturated NaCl. The organic layer was dried over MgSO$_4$. After the removal of volatiles, the residue was chromatographed on silicagel using hexanes-ethylacetate (7:3), then hexanes-ethylacetate (55:45) to yield pure product as white solid (2.629 g, 74% yield). $^1$H NMR (360 MHz, CDCl$_3$) δ 7.76 (d, J=8.2 Hz, 2H), 7.34 (d, J=8.2 Hz, 2H), 5.88 (d, J=3.8 Hz, 1H), 4.51 (d, J=3.8 Hz, 1H), 4.38–4.28 (m, 3H), 4.14 (td, J=9.4, 6.8 Hz, 1H), 2.46 (s, 3H), 1.46 (s, 3H), 1.30 (s, 3H).

Example 20

1,2-Isopropylidene-5-deoxy-5-N-allylamino-α-D-xylofuranose

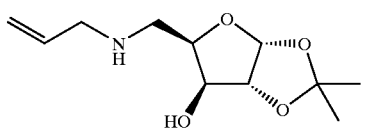

To a stirred solution of 1,2-Isopropylidene-5-p-toluenesulfonyl-α-D-xylofuranose (Example,19) (590 mg, 1.71 mmol) in acetonitrile (4 mL) was added allyl amine (1.3 mL, 17.3 mmol). Reaction mixture was refluxed overnight. Saturated NaHCO$_3$ was added to the reaction mixture, followed by extraction with EtOAc. The combined organic layer was dried over MgSO$_4$. After the removal of volatiles, the residue was chromatographed on silicagel using hexanes-ethylacetate (1:1), then MeOH-dichloromethane (15:75) to yield pure product (388 mg, 99% yield). $^1$H NMR (360 MHz, MeOD-d$_4$) δ 5.90–5.87 (m, 2H), 5.27–5.10 (m, 2H), 4.46 (d, J=3.8 Hz, 1H), 4.25–4.17 (m, 1H), 4.08 (d, J=2.8 Hz, 1H), 3.29–3.23 (m, 2H), 2.96–2.84 (m, 2H), 1.44 (s, 3H), 1.28 (s, 3H).

Example 21

(2R, 3S, 4S, 5R)-N-Allyl-2-trans-β-Styryl-3,4,5-trihydroxy-piperidine

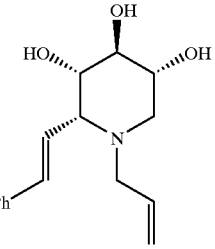

To the 0° C. solution of 1,2-Isopropylidene-5-deoxy-5-N-allylamino-α-D-xylofuranose (Example 20)(119 mg, 0.52 mmol) in dichloromethane (0.5 mL) was added dropwise cold mixture of trifluoroacetic acid-H$_2$O (8:2, 1.0 mL). Reaction mixture was warmed up to room temperature and stirred for one day. The reaction mixture was evaporated under high vacuum without heating, and kept under vacuum for about 1 h. EtOH (4 mL) was added to the residue, followed by the addition of (E)-2-phenylethenyl boronic acid (77 mg, 0.52 mmol). After stirring for 6 h, the volatile was removed. The residue was diluted with EtOAc, extracted with 6N HCl several times. The combined acid layer was cooled 0° C., neutralized with 6N NaOH until basic, followed by extraction with EtOAc. The combined organic layer was dried over MgSO$_4$, followed by evaporation. The residue was chromatographed on silicagel using methanol-dichloromethane (5:95), then methanol-dichloromethane (1:9) to yield pure product (54 mg, 38% yield). $^1$H NMR (360 MHz, MeOD-d$_4$) δ 7.47–7.14 (m, 5H, $H_{14,14',15,15',16}$), 6.58 (d, $J_{13,12}$=15.6 Hz, 1H, $H_{13}$), 6.40 (dd, $J_{12,13}$=15.6 Hz, $J_{12,2}$=9.8 Hz, 1H, $H_{12}$), 5.92–5.78 (m, 1H, $H_9$), 5.21–5.11 (m, 2H, $H_{10,11}$), 3.68 (dd, $J_{3,4}$=8.6 Hz, $J_{3,2}$=5.0 Hz, 1H, $H_3$), 3.65–3.53 (m, 3H, $H_{5,4,2}$), 3.21–3.03 (m, 2H, $H_{7,8}$), 2.79 (dd, $J_{6a,5}$=11.8 Hz, $J_{6a,6b}$=4.2 Hz, 1H, $H_{6a}$), 2.59 (dd, $J_{6b,6a}$=11.8 Hz, $J_{6b,5}$=8.7 Hz, 1H, $H_{6b}$).

Example 22

(2R, 3S, 4S, 5R)-N-Allyl-2-trans-β-Styryl-3,4,5-triacetoxypiperidine

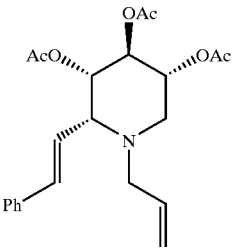

To the suspension of (2R, 3S, 4S, 5R)-N-Allyl-2-trans-β-Styryl-3,4,5-trihydroxy-piperidine (Example 21) (55.5 mg, 0.2 mmol) in dichloromethane (2 mL) was added DMAP (15 mg, 0.12 mmol), Et$_3$N (126.4 μL, 0.91 mmol), Ac$_2$O (85.6 μL, 0.91 mmol). The suspension became clear. After stirring for 1 h, the solution was diluted with EtOAc, washed with saturated NaHCO$_3$, brine, dried over MgSO$_4$. After the removal of volatiles, the residue was chromatographed on silicagel using hexanes-ethylacetate (7:3) to yield pure product (77.4 mg, 96% yield). HCl salt of the product was made by dissolving the product in Et$_2$O, adding excess 1N HCl in Et$_2$O, followed by evaporation. [α]$_D$=+140.5° (C=2.26, CHCl$_3$);

$^1$H NMR (500 MHz, CDCl$_3$) δ 7.46–7.24 (m, 5H), 6.49 (d, J=15.7 Hz, 1H), 6.36 (dd, J=15.7, 9.9 Hz, 1H), 5.85–5.73 (m, 1H), 5.39 (t, J=9.7 Hz, 1H), 5.20–5.12 (m, 2H), 5.08–5.00 (m, 2H), 3.92 (dd, J=9.7, 5.7 Hz, 1H), 3.21 (dd, J=13.9, 6.1 Hz, 1H), 3.05 (dd, J=13.8, 6.3 Hz, 1H), 2.97 (dd, J=11.8, 5.8 Hz, 1H), 2.63 (t, J=10.8 Hz, 1H), 2.05 (s, 3H), 2.04 (s, 3H), 1.96 (s, 3H).

Example 23

(6R, 7S, 8S, 8aR)-1,2-Dehydro-6,7,8-triacetoxyindolizidine

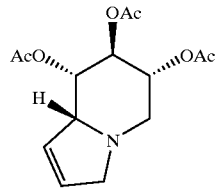

To the solution of HCl salt of 2R, 3S, 4S, 5R)-N-Allyl-2-trans-β-Styryl-3,4,5-triacetoxypiperidine (Example 22) (0.19 mmol) in dicholoromethane (6 mL) was added Grubb's catalyst (32 mg, 0.039 mmol). The reaction mixture was stirred under argon for two days. The flask was opened to the air for 6 h before the addition of 0.1N NaOH. The mixture was extracted with EtOAc, and the combined organic layer was dried over MgSO$_4$. After the removal of volatiles, the residue was chromatographed on silicagel using MeOH-dichloromethane (2:98) to yield 47 mg of product plus some impurity, collecting one clean tube for analytic purpose. $^1$H NMR (360 MHz, MeOD-d$_4$) δ 6.00–5.95 (m, 1H), 5.72–5.66 (m, 1H), 5.07–5.04 (m, 1H), 4.99–4.92(m, 2H), 3.93–3.87 (m, 1H), 3.62–3.49 (m, 2H), 3.11 (dd, J=11.7, 3.4 Hz, 1H), 2.59 (dd, J=11.7, 6.8 Hz, 1H), 2.08 (s, 3H), 2.06 (s, 3H), 2.04 (s, 3H).

Example 24

(6R, 7S, 8S, 8aR)-1,2-Dehydro-6,7,8-trihydroxyindolizidine

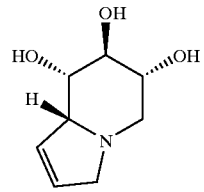

To the solution of 6R, 7S, 8S, 8aR)-1,2-Dehydro-6,7,8-triacetoxyindolizidine (Example 23) in MeOH (5 mL) and H$_2$O (0.1 mL) was added K$_2$CO$_3$ (221 mg, 1.58 mmol). The reaction mixture was stirred for 5 h. The solid was filtered, washed with MeOH, followed by evaporation of the volatiles. MeOH was added, and the solid was filtered. After the removal of volatiles, the residue was chromatographed on silicagel using EtOAc-MeOH—NH$_4$OH (80:15:5) to yield pure product (23.5 mg, 71% yield from 6). [α]$_D$=+68.7° (C=1.01, MeOH); $^1$H NMR (500 MHz, MeOD-d$_4$) δ 5.99–5.94 (m, 1H), 5.89–5.84 (m, 1H), 3.79 (t, J=3.3 Hz, 1H), 3.77–3.73 (m, 1H), 3.66 (t, J=4.3 Hz, 1H), 3.65–3.60 (m, 1H), 3.60–3.54 (m, 1H), 3.49–3.42 (m, 1H), 2.95 (dd, J=11.2, 3.1 Hz, 1H), 2.84 (dd, J=11.2, 5.9 Hz, 1H).

Example 25

(6R, 7S, 8S, 8aR)-6,7,8-Trihydroxyindolizidine

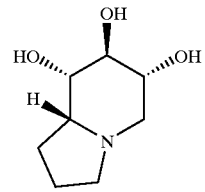

To the solution of (6R, 7S, 8S, 8aR)-1,2-Dehydro-6,7,8-trihydroxyindolizidine (Example 24) (33 mg, 0.19 mmol) in MeOH (6 mL) was added hydrogen chloride in Et$_2$O (1N, 0.8 mL), and Pd/C catalyst (5% wt, 82 mg). The reaction mixture was stirred under the atmosphere of hydrogen gas for 2 h. Reaction mixture was filtered through celite pad and volatiles were removed. Pure product was isolated by flash chromatography on silica gel using EtOAC-MeOH—NH$_4$OH (80:15:5) as an eluent (25.5 mg, 76% yield). [α]$_D$=−27.0° (C=1.02, MeOH). [reported for the enantiomeric compound [α]$_D$=+23.00 (C=0.72, MeOH)$^{18}$] $^1$H NMR (360 MHz, MeOD-d$_4$) δ 3.82 (t, J=3.5 Hz, 1H), 3.71–3.66 (m, 2H), 3.02–2.91 (m, 2H), 2.55–2.42 (m, 2H), 2.21 (dd, J=17.3, 8.7 Hz, 1H), 1.96–1.62 (m, 4H).

Example 26

(1S,2S,6R,7S,8R,8aR)-1,2-Dihydroxy-6,7,8-triacetoxyindolizidine

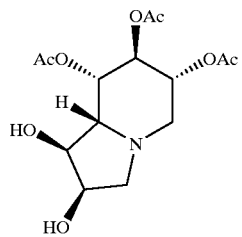

To the solution of (6R, 7S, 8S, 8aR)-1,2-Dehydro-6,7,8-triacetoxyindolizidine (Example 23) (70.7 mg, 0.24 mmol) in acetone (3 mL) and H$_2$O (0.5 mL) was added 4-methylmorpholine-N-oxide (32 mg, 0.26 mmol), OsO$_4$ (2.5% wt, 30 μL, 0.0024 mmol). The reaction mixture was stirred for one day. After the removal of volatiles, the residue was chromatographed on silica gel using MeOH-dichloromethane (5:95) to yield single diastereomer (5.74) (57.2 mg, 51% overall yield from (5.70)). [α]$_D$=−65.4° (C=1.14, MeOH). $^1$H NMR (500 MHz, MeOD-d$_4$) δ 5.05–4.97 (m, 2H, H$_7$, H$_8$), 4.84–4,79 (m, 1H, H$_6$), 4.11 (ddd, J$_{2,1}$=7.4 Hz, J$_{2,3b}$=6.6 Hz, J$_{2,3a}$=5.0 Hz, H$_2$), 3.83 (dd, J$_{1,8a}$=8.4 Hz, J$_{1,2}$=7.4 Hz, H$_1$), 3.45 (dd, J$_{3b,3a}$=10.0 Hz, J$_{3b,2}$=6.6 Hz, H$_{3b}$), 3.07 (dd, J$_{5b,5a}$=12.9 Hz, J$_{5b,6}$=1.3 Hz, H$_{5b}$), 2.58 (dd, J$_{5a,5b}$=12.9 Hz, J$_{5a,6}$=2.3 Hz, H$_{5a}$), 2.54 (dd, J$_{8a,1}$=8.4 Hz, J$_{8a,8}$=1.2 Hz, H$_{8a}$), 2.21 (dd, J$_{3a,3b}$=10.0 Hz, J$_{3a,2}$=5.0 Hz, H$_{3a}$), 2,11 (s, 3H), 2.10 (s, 3H), 2.07 (s, 3H).

Example 27

(1s,2S,6R,7S,8R,8aR)-1,2,6,7,8-Pentahydroxyindolizidine

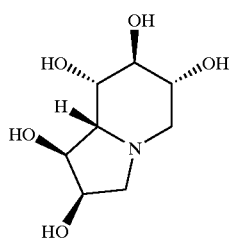

Prepared analogously to Example 25 and purified by H⁺ ion exchange resin, in 99% yield. $[\alpha]_D = -75.6°$ (C=1.04, MeOH). ¹H NMR (360 MHz, MeOD-$d_4$) δ 4.16–4.04 (m, 2H), 3.92–3.86 (m, 2H), 3.78–3.73 (m, 1H), 3.47 (dd, J=10.4, 6.3 Hz, 1H), 3.01 (dd, J=11.8, 2.1 Hz, 1H), 2.74 (dd, J=11.8, 1.6 Hz, 1H), 2.66(d, J=8.2 Hz, 1H), 2.38 (dd, J=10.4, 4.6 Hz, 1H).

Example 28

1,2-Isopropylidene-5-deoxy-5-N-benzylamino-α-D-xylofuranose

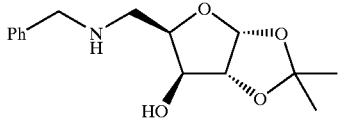

Prepared analogously to Example 20 in 96% yield. ¹H NMR(360 MHz, MeOD-$d_4$) δ 7.36–7.18 (m, 5H), 5.88 (d, J=3.2 Hz, 1H), 4.45 (d, J=3.6 Hz, 1H), 4.25–4.18 (m, 1H), 4.08 (d, J=2.0 Hz, 1H), 3.83–3.71 (m, 2H), 2.98–2.85 (m, 2H), 1.43 (s, 3H), 1.27 (s, 3H).

Example 29

(2R, 3S, 4S, 5R)-N-Benzyl-2-trans-β-Styryl-3,4,5-trihydroxy-piperidine

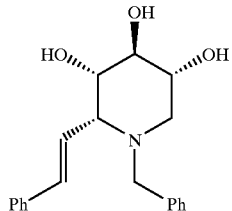

Prepared analogously to Example 21 from the product of Example 28 in 30% yield. ¹H NMR (360 MHz, MeOD-$d_4$) δ 7.46–7.15 (m, 10H), 6.52–6.44 (m, 2H), 3.70 (dd, J=9.3, 5.2 Hz, 1H), 3.66–3.49 (m, 5H), 2.74 (dd, J=11.6, 4.7 Hz, 1H), 2.63(dd, J=11.6, 9.2 Hz, 1H).

Example 30

1,2-Isopropylidene-5-deoxy-5-N-homoallylamino-α-D-xylofuranose

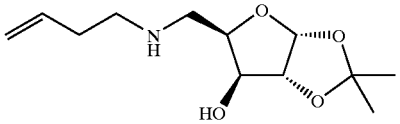

Prepared analogously to Example 20 in 67% yield based on consumed starting material. ¹H NMR (360 MHz, MeOD-$d_4$) δ 5.88 (d, J=3.5 Hz, 1H), 5.85–5.72 (m, 1H), 5.13–4.98 (m, 2H), 4.45 (d, J=3.6 Hz, 1H), 4.22–4.16 (m, 1H), 4.08 (d, J=2.3 Hz, 1H), 3.00–2.84 (m, 2H), 2.75–2.59 (m, 2H), 2.30–2.20 (m, 2H), 1.43 (s, 3H), 1.28 (s, 3H).

Example 31

(2R, 3S, 4S, 5R)-N-Homoallyl-2-trans-β-Styryl-3,4,5-trihydroxypiperidine

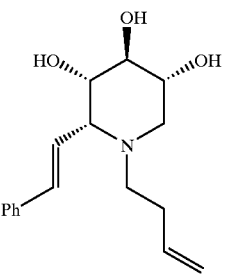

Prepared analogously to Example 21 in 31% yield. ¹H NMR (360 MHz, MeOD-$d_4$) δ 7.45–7.37 (m, 2H), 7.34–7.17 (m, 3H), 5.85–5.70 (m, 1H), 5.08–4.92 (m, 2H), 3.66 (dd, J=8.5, 4.9 Hz, 1H), 3.63–3.52 (m, 3H), 2.82 (dd, J=12.0, 4.7 Hz, 1H), 2.68–2.44 (m, 3H), 2.34–2.15 (m, 2H).

Example 32

(2R, 3S, 4S, 5R)-N-Homoallyl-2-trans-β-Styryl-3,4,5-triacetoxypiperidine

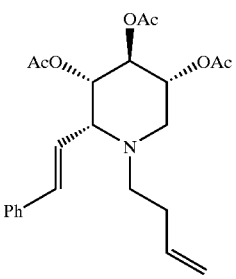

Prepared analogously to Example 22 from the product of Example 31 in 99% yield. $[\alpha]_D = +106.8°$ (C=2.09, CHCl₃); ¹H NMR (500 MHz, CDCl₃) δ 7.45–7.24 (m, 5H), 6.52 (d, J=15.6 Hz, 1H), 6.38 (dd, J=15.6, 9.6 Hz, 1H), 5.82–5.71 (m, 1H), 5.38 (t, J=9.8 Hz, 1H), 5.09–4.97 (m, 4H), 3.91 (dd, J=9.4, 5.5 Hz, 1H), 2.99 (dd, J=11.7, 5.5 Hz, 1H), 2.69 (t, J=11.0 Hz, 1H), 2.67–2.60 (m, 1H), 2.50 (dt, J=12.7, 7.1 Hz, 1H), 2.22 (q, J=7.1 Hz, 2H), 2.05 (s, 6H), 1.96 (s, 3H).

Example 33

(1S,2S,3R,9aR)-8,9-dehydro-1,2,3-Trihydroxyquinolizidine

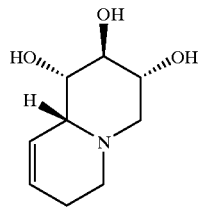

Prepared analogously to Example 24 from the product of Example 32 in 61% overall yield of two steps. $[\alpha]_D = -24.9°$ (C=1.13, MeOH); $^1$H NMR (360 MHz, MeOD-d$_4$) δ 5.87–5.79 (m, 1H), 5.62–5.51 (m, 1H), 3.76–3.61 (m, 2H), 3.59–3.54 (m, 1H), 3.26–3.10 (m, 1H), 2.83 (dd, J=11.6, 6.0 Hz, 1H), 2.78 (dd, J=12.0, 4.5 Hz, 1H), 2.68 (dd, J=12.0, 2.4 Hz, 1H), 2.66–2.50 (m, 1H), 2.49–2.35 (m, 1H), 2.03–1.90 (m, 1H).

Example 34

(1S, 2S, 3R, 9aR)-1,2,3-Trihydroxyquinolizidine

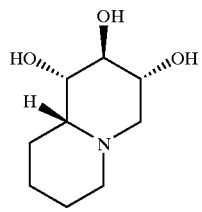

Prepared analogously to Example 25 in 70% yield. $^1$H NMR (360 MHz, MeOD-d$_4$) δ 3.82–3.74 (m, 1H), 3.72–3.65 (m, 1H), 3.45–3.40 (m, 1H), 2.89–2.81 (m, 1H), 2.79 (dd, J=11.4, 9.2 Hz, 1H), 2.59 (dd, J=12.1, 2.1 Hz, 1H), 2.46–2.30 (m, 1H), 2.28–2.10 (m, 1H), 1.88–1.53 (m, 4H), 1.49–1.30 (m, 2H).

Example 35

(2S,3S,4S,5R)-N-Allyl-2-furanyl-3,4,5-trihydroxypiperidine

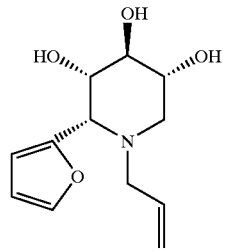

Prepared analogously to Example 21 in 60% yield. $^1$H NMR (360 MHz, MeOD-d$_4$) δ 7.50 (d, $J_{14,13}$=1.8 Hz, 1H, H$_{14}$), 6.39 (dd, $J_{13,12}$=3.0 Hz, $J_{13,14}$=1.8 Hz, 1H, H$_{13}$), 6.31 (d, $J_{12,13}$=3.0 Hz, 1H, H$_{12}$), 5.86–5.71 (m, 1H, H$_9$), 5.17–5.05 (m, 2H, H$_{10,11}$), 4.17 (d, $J_{2,3}$=5.8 Hz, 1H, H$_2$), 3.88 (t, $J_{4,3}$=$J_{4,5}$=9.1 Hz, 1H, H$_4$), 3.77 (dd, $J_{3,4}$=9.1 Hz, $J_{3,2}$=5.8 Hz, 1H, H$_3$), 3.61 (ddd, $J_{5,6b}$=10.9 Hz, $J_{5,4}$=9.1 Hz, $J_{5,6a}$=5.5 Hz, 1H, H$_5$), 3.02 (dd, J=13.5 Hz, 6.6 Hz, 1H, H$_7$), 2.85–2.77 (m, 1H, H$_8$), 2.78 (dd, $J_{6a,6b}$=10.9 Hz, $J_{6a,5}$=5.5 Hz, 1H, H$_{6a}$), 2.59 (t, $J_{6b,6a}$=$J_{6b,5}$=10.9 Hz, 1H, H$_{6b}$).

Example 36

(2S,3S,4S,5R)-N-Allyl-2-furanyl-3,4,5-triacetoxypiperidine

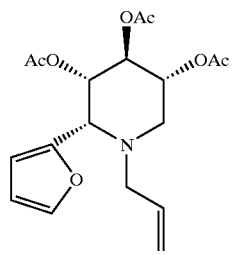

Prepared analogously to Example 22 in quantitative yield. $^1$H NMR (500 MHz, CDCl$_3$) δ 7.50 (d, J=1.8 Hz, 1H), 6.36 (dd, J=3.0, 1.8 Hz, 1H), 6.25 (d, J=3.0 Hz, 1H), 5.80–5.70 (m, 1H), 5.77 (t, J=9.8 Hz, 1H), 5.17–5.02 (m, 4H), 4.45 (d, J=6.6 Hz, 1H), 3.09 (dd, J=13.5, 6.6 Hz, 1H), 2.97–2.88 (m, 2H), 2.72 (t, J=10.9 Hz, 1H), 2.05 (s, 3H), 2.04 (s, 3H), 1.87 (s, 3H).

Example 37

(2S,3S,4S,5R)-2-furanyl-3,4,5-triacetoxypiperidine

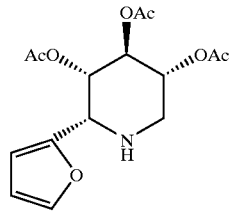

10 mL vacuum dried flask containing the product of Example 36 (212 mg, 0.58 mmol), Pd(PPh$_3$)$_4$ (14 mg, 0.012 mmol), N,N'-dimethylbarbituric acid (275 mg, 1.74 mmol) was purged under argon. Dichloromethane (2.9 mL) was added. The reaction mixture was stirred at 35° C. overnight. A large amount of EtOAc was added, washed with aqueous Na$_2$CO$_3$ several times. The organic layer was dried over MgSO$_4$. After the removal of volatiles, the residue was chromatographed on silicagel using hexanes-EtOAc (1:1) to yield pure product (189 mg, 100% yield). $^1$H NMR (360 MHz, CDCl$_3$) δ 7.38–7.33 (m, 1H), 6.33–6.27 (m, 2H), 5.44 (t, J=7.7 Hz, 1H), 5.02 (dd, J=7.7, 4.7 Hz, 1H), 4.79 (td, J=7.7, 4.7 Hz, 1H), 4.46 (d, J=4.7 Hz, 1H), 3.10 (dd, J=13.1, 4.7 Hz, 1H), 2.84 (dd, J=13.1, 7.7 Hz, 1H), 2.04 (s, 3H), 2.00 (s, 3H), 1.93 (s, 3H).

Example 38

(2S,3S,4S,5R)-N-Benzyloxycarbonyl-2-furanyl-3,4,5-triacetoxypiperidine

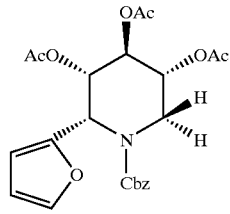

To the solution of the product of Example 37 (189 mg, 0.58 mmol) in dichloromethane (2.5 mL) was added Et$_3$N (0.10 mL, 0.72 mmol), and the mixture was cooled to 0° C. CbzCl (0.11 mL, 0.73 mmol) was added dropwise, and the solution was warmed up room temperature for 2 h. The reaction was quenched with aqueous NaCl, extracted with dichloromethane several times. The combined organic layer was dried over MgSO$_4$. After the removal of volatiles, the residue was chromatographed on silica gel using hexanes-EtOAc (3:1) and hexanes-EtOAc (1:1) to yield pure product (138 mg) and starting material (5.81) (75 mg), 86% yield based on the consumed (5.81). Contain two rotamers at rt. $^1$H NMR (360 MHz, MeOD-d$_4$) δ 7.55–7.48 (m, 1H), 7.38–7.21 (m, 5H), 6.50–6.33 (m, 2H), 5.90 (d, J$_{2,3}$=5.7 Hz, 0.5H, H$_2$), 5.87 (d, J$_{2,3}$=5.7 Hz, 0.5H, H$_2$), 5.76 (t, J$_{4,3}$=J$_{4,5}$=9.6 Hz, 0.5H, H$_4$), 5.74 (t, J$_{4,3}$=J$_{4,5}$=9.6 Hz, 0.5H, H$_4$), 4.99 (ddd, J$_{5,6b}$=10.9 Hz, J$_{5,4}$=9.6 Hz, J$_{5,6a}$=5.6 Hz, H$_5$), 4.39 (dd, J$_{6a,6b}$=13.0 Hz, J$_{6a,5}$=5.6 Hz, 0.5H, H$_{6a}$), 4.35 (dd, J$_{6a,6b}$=13.0 Hz, J$_{6a,5}$=5.6 Hz, 0.5H, H$_{6a}$), 3.07 (dd, J$_{6b,6a}$=13.0 Hz, J$_{6b,5}$=10.9 Hz, 0.5H, H$_{6b}$) 2.97 (dd, J$_{6b,6a}$=13.0 Hz, J$_{6b,5}$=10.9 Hz, 0.5H, H$_{6b}$), 2.00 (s, 3H), 1.99 (s, 3H), 1.87 (s, 3H).

Example 39

(2S,3S,4S,5R)-N-Benzyloxycarbonyl-3,4,5-triacetoxypiperidine-2-carboxylic acid

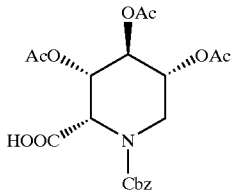

To a well stirred solution of NaIO$_4$ (370 mg, 1.73 mmol) in H$_2$O—CCl$_4$—CH$_3$CN (3:2:3, 8 mL) was added RuCl$_3$ (3.0 mg, 0.014 mmol). After 15 min stirring, (5.82) (132 mg, 0.2.9 mmol) in CH$_3$CN (1.0 ml) was added. The color of the solution turned instantaneously from yellowish to black. Then enough NaIO$_4$ was added to restore the yellowish color. After 5 min, the volatile were evaporated. The residue was purified by flash chromatography using MeOH-DCM (1:9) to give pure product (75.1 mg, 60% yield). Contain two rotamers at rt. $^1$H NMR (360 MHz, MeOD-d$_4$+CDCl$_3$) δ 7.39–7.21 (m, 5H), 5.62 (t, J=9.4 Hz, 1H), 5.15–5.09 (m, 2H), 5.05 (d, J=6.7 Hz, 1H), 4.95 (dd, J=9.4, 6.7 Hz, 1H), 4.90–4.80 (m, 1H), 4.40–4.25 (m, 1H), 3.70–3.55 (m, 1H), 2.02 (s, 3H) 2.00 (s, 6H).

Example 40

(2S,3S,4S,5R)-N-Benzyloxycarbonyl-3,4,5-trihydroxypiperidine-2-carboxylic acid

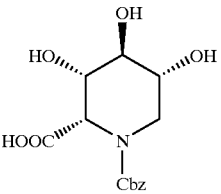

Prepared analogously to Example 27 in 88% yield. [α]$_D$=−5.0° (C=1.10, MeOH); Contain two rotamers at rt. $^1$H NMR (500 MHz, MeOD-d$_4$) δ 7.45–7.20 (m, 5H), 5.14 (t, J=12.4 Hz, 1H), 5.11–5.04 (m, 1H), 4.80 (d, J=5.9 Hz, 0.54H), 4.74 (d, J=5.2 Hz, 0.46H), 4.16–4.03 (m, 1H), 3.52–3.43(m, 1H), 3.43–3.31 (m, 2H), 3.03–2.86 (m, 1H).

Example 41

(2S,3S,4S,5R)-3,4,5-Trihydroxypipecolic acid

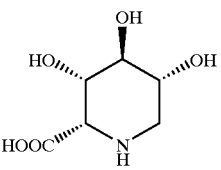

To the solution of 2S,3S,4S,5R)-N-Benzyloxycarbonyl-3,4,5-trihydroxypiperidine-2-carboxylic acid (Example 40) (41.7 mg, 0.14 mmol) in MeOH (4 mL) was added Pd/C catalyst (5% wt, 60 mg). The reaction mixture was stirred under the atmosphere of hydrogen gas for 6 h. Catalyst was filtered through celite pad and volatiles were removed. Pure product was isolated by flash chromatography on silicagel using H$_2$O-MeOH (2:98) as an eluent (16.7 mg, 72% yield). [α]$_D$=−8.6° (C=0.21, H$_2$O). $^1$H NMR (360 MHz, D$_2$O+ two drops of MeOD-d$_4$) δ 4.09–4.00 (m, 1H), 3.89–3.75 (m, 3H), 3.23 (dd, J=13.1, 1.9 Hz, 1H), 3.08 (dd, J=13.1, 3.8 Hz, 1H);

$^{13}$C NMR (125 MHz, D$_2$O+ two drops of MeOD-d$_4$) δ 175.3, 71.1, 70.5, 68.3, 59.1, 46.2.

Example 42

Methyl 2,3-O-isopropylidene-D-lyxofuranoside

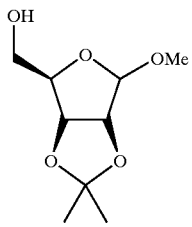

To D-lyxose (1.0 g, 6.66 mol) in acetone (5 mL) and MeOH (5 mL) was added concentrated HCl (0.1 mL), and the solution was refluxed for 22 h. The reaction was cooled, neutralized with saturated NaHCO$_3$, and extracted with Et$_2$O and dichloromethane until no product was in aqueous layer. The combined organic layer was dried over with MgSO$_4$, and evaporated. Pure product was isolated by flash chromatography on silicagel using Et₂O: hexanes (2:1) as an eluent (0.925 g, 68% yield). ¹H NMR (360 MHz, CDCl₃) δ 4.53–4.48 (m, 1H), 4.35 (dd, J=5.8, 3.6 Hz, 1H), 4.18 (d, J=5.8 Hz, 1H), 3.63 (dd, J=9.2, 5.3 Hz, 1H), 3.57–3.34 (m, 2H), 2.92 (s, 3H), 1.05 (s, 3H), 0.89 (s, 3H).

Example 43

Methyl 5-N-Allyl-5-deoxy-2,3-isopropylidene-D-pentoaldo-1-furanoside

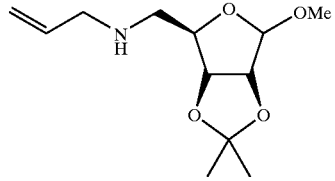

To the solution of dichloromethane (35 mL) and pyridine (2.23 mL, 27.57 mmol) was added CrO₃ (1.390 g, 13.76 mmol) over 15 min. To the resultant red solution was added dropwise methyl 2,3-O-isopropylidene-D-lyxofuranoside (Example 42)(234.2 mg, 1.15 mmol) in dichloromethane (5 mL), and the reaction mixture was stirred for 1 h. The organic layer was decanted and poured into cold saturated NaHCO3, the organic layer was separated, and the aqueous layer was extracted with dichloromethane. The combined organic layer was dried over MgSO4 and evaporated. The residue was azeotroped with toluene (3×10 mL), redissolved in dichloromethane, treated with silicagel (2 g). The solution was filtered through a pad of celite and flushed with dichloromethane, and the eluant was evaporated to yield crude product (170.3 mg), which went on to the next step without further purification. ¹H NMR(360 MHz, CDCl₃) δ 9.66 (s, 1H), 5.11–5.05 (m, 2H), 4.61 (d, J=6.0 Hz, 1H), 4.39–4.35 (m, 1H), 3.37 (s, 3H), 1.43 (s, 3H), 1.29 (s, 3H). To the solution of crude product of the above reaction (170.3 mg) in MeOH (5 mL) was added allylamine (0.1 ml, 1.33 mmol), and the reaction mixture was stirred for 5 h. NaBH₄ (52 mg, 1.35 mmol) was added to the reaction mixture, and stirred for 30 min. 1N NaOH was added to the reaction mixture, and the aqueous layer was extracted with DCM until no product was observed in the aqueous layer. The combined organic layer was dried over MgSO₄, and evaporated. The residue was purified by flash chromatography using hexanes-EtOAc (1:1) and MeOH-DCM (1:9) to give pure product (111.4 mg, 40% overall yield ). ¹H NMR (360 MHz, CDCl₃) δ 5.99–5.85 (m, 1H), 5.24–5.16 (m, 1H), 5.14–5.08(m, 1H), 4.90–4.87 (brs, 1H), 4.70 (dd, J=6.1, 3.8 Hz, 1H), 4.56 (d, J=5.9 Hz, 1H), 4.12–4.05 (m, 1H), 3.32 (s, 3H), 3.34–3.29 (m, 2H), 2.94 (d, J=6.3 Hz, 2H), 1.45 (s, 3H), 1.31 (s, 3H); ¹³C NMR (90 MHz, CDCl₃) δ 136.4, 116.0, 112.2, 106.8, 84.9, 79.9, 78.9, 54.3, 52.4, 47.6, 25.9, 24.7.

Example 44

(2S,3R,4S,5R)-N-Allyl-2-trans-β-Styryl-3,4,5-trihydroxypiperidine

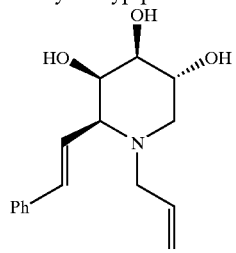

Prepared analogously to Example 21 from the product of Example 43 in 18% yield, not optimized. ¹H NMR (360 MHz, MeOD-d₄) δ 7.46–7.16 (m, 5H, H₁₄,₁₄',₁₅,₁₅',₁₆) 6.62 (d, J₁₃,₁₂=16.0 Hz, H₁₃) 6.41 (dd, J₁₂,₁₃=16.0 Hz, J₁₂,₂=9.1 Hz, H₁₂), 5.98–5.82 (m, H₉), 5.21–5.09 (m, 2H, H₁₀,₁₁), 3.87 (ddd, J₅,₆b=10.4 Hz, J₅,₄=9.4 Hz, J₅,₆a=4.8 Hz, H₅), 3.78 (dd, J₃,₄=3.1 Hz, J₃,₂=1.7 Hz, H₃), 3.37 (dddd, J₇,₈=13.8 Hz, 3.1 Hz, H₄), 3.08 (dd, J₆a,₆b=11.3 Hz, J₆a,₅=4.8 Hz, H₆a), 2.93 (dd, J₂,₁₂=9.1 Hz, J₂,₃=1.7 Hz, H₂), 2.80 (dd, J₈,₇=13.8 Hz, J₈,₉=8.1 Hz, H₈), 1.94 (dd, J₆b,₆a=11.3 Hz, J₆b,₅=10.4 Hz, H₆b).

Example 45

1,2-Isopropylidene-5-p-toluenesulfonyl-β-D-arabinofuranose

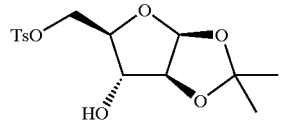

Prepared analogously to Example 19 in 45% yield. ¹H NMR (500 MHz, CDCl₃) δ 7.80 (d, J=8.2 Hz, 2H), 7.36 (d, J=8.2 Hz, 2H), 5.89 (d, J=4.1 Hz, 1H), 4.52 (d, J=3.6 Hz, 1H), 4.27 (brs, 1H), 4.20–4.09 (m, 3H), 3.09 (brs, 1H), 2.44 (s, 3H), 1.34 (s, 3H), 1.27 (s, 3H).

Example 46

1,2-Isopropylidene-5-deoxy-5-N-allylamino-β-D-arabinofuranose

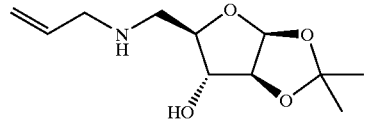

Prepared analogously to Example 20 from the product of Example 45 in 70% yield. ¹H NMR (360 MHz, MeOD-d₄) δ 5.96–5.82 (m, 1H), 5.90 (d, J=3.7 Hz, 1H), 5.27–5.12 (m, 2H), 4.51 (d, J=4.2 Hz, 1H), 4.10 (ddd, J=9.7, 4.4, 1.8 Hz, 1H), 4.04–4.02 (m, 1H), 3.30–3.25 (m, 2H), 2.91 (dd, J=12.3, 9.6 Hz, 1H), 2.75 (dd, J=12.3, 4.6 Hz, 1H) 1.47 (s, 3H), 1.29 (s, 3H).

Example 47

(2S,3R,4R,5R)-N-Allyl-2-trans-β-Styryl-3,4,5-trihydroxypiperidine

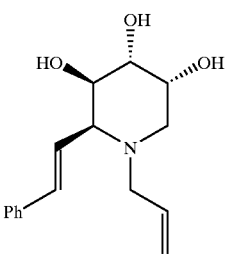

Prepared analogously to Example 21 from the product of Example 46 in 60% yield. ¹H NMR (500 MHz, MeOD-d₄) δ 7.41 (d, J=7.5 Hz, H₁₄,₁₄'), 7.25 (t, J=7.5 Hz, H₁₅,₁₅'), 7.19 (d, J=7.5 Hz, H₁₆), 6.60 (d, J₁₃,₁₂=16.4 Hz, H₁₃), 6.39 (dd, J₁₂,₁₃=16.4 Hz, J₁₂,₂=9.6 Hz, H₁₂), 5.96–5.85 (m, H₉), 5.20–5.10 (m, H₁₀,₁₁), 4.05 (ddd, J₅,₆b=9.4 Hz, J₅,₆a=4.3 Hz, J₅,₄=3.3 Hz H₅), 3.86 (dd, J₄,₃=4.5 Hz, J₄,₅=3.3 Hz, H₄), 3.78

(dd, $J_{3,4}$=4.5 Hz, $J_{3,2}$=2.3 Hz, $H_3$), 3.31 (dd, $J_{2,12}$=9.6 Hz, $J_{2,3}$=2.3 Hz, $H_1$), 3.30–3.26 (m, $H_7$), 2.89 (dd, J=13.5, 7.9 Hz, $H_8$), 2.80 (dd, $J_{6a,6b}$=11.0 Hz, $J_{6a,5}$=4.3 Hz, $H_6$), 2.44 (dd, $J_{6b,6a}$=11.0 Hz, $J_{6b,5}$=9.4 Hz, $H_{6b}$).

A number of embodiments of the invention have been described. Nevertheless, it will be understood that various modifications may be made without departing from the spirit and scope of the invention. Accordingly, other embodiments are within the scope of the following claims.

What is claimed is:

1. A compound of formula

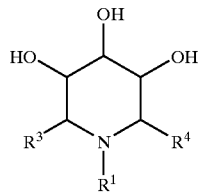

wherein:

$R^1$ is hydrogen, alkyl, aryl, heteroaryl, hydroxy, or alkoxy;

$R^3$ is aryl, heteroaryl, alkenyl, or alkynyl, or $R^1$ and $R^3$ can be joined to form a ring of 5 to 10 atoms;

$R^4$ is hydrogen, alkyl, aryl, heteroaryl, alkenyl, alkynyl, acyl, carboxy, or carboxamido.

2. The compound of claim 1, wherein: the compound has a formula selected from the following:

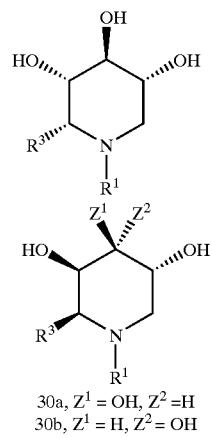

30a, $Z^1$ = OH, $Z^2$ =H
30b, $Z^1$ = H, $Z^2$ = OH

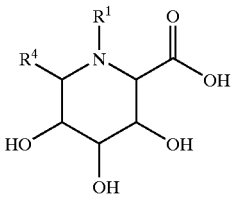

31

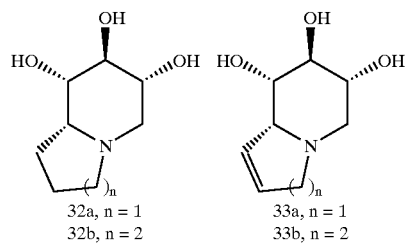

32a, n = 1
32b, n = 2

33a, n = 1
33b, n = 2

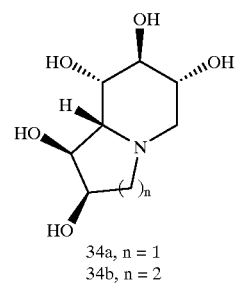

34a, n = 1
34b, n = 2 wherein $R^1$ is hydrogen, alkyl, aryl, heteroaryl, hydroxy, or alkoxy;

$R^3$ is aryl, heteroaryl, alkenyl or alkynyl; and $R^4$ is hydrogen, alkyl, aryl, heteroaryl, alkenyl, alkynyl, acyl, carboxy, or carboxamido.

3. The compound of claim 1, wherein:

$R^3$ is aryl, heteroaryl, or alkenyl, and $R^4$ is hydrogen.

* * * * *